US010161925B2

(12) United States Patent
Merali et al.

(10) Patent No.: US 10,161,925 B2
(45) Date of Patent: Dec. 25, 2018

(54) DETECTION OF HIV-1-ASSOCIATED NEUROCOGNITIVE DISORDERS

(71) Applicants: Temple University-Of The Commonwealth System of Higher Education, Philadelphia, PA (US); The Johns Hopkins University, Baltimore, MD (US)

(72) Inventors: Salim Merali, Bryn Mawr, PA (US); Carlos A. Barrerro, Philadelphia, PA (US); Kamel Khalili, Bala Cynwyd, PA (US); Jay Rappaport, Somers Point, NJ (US); Norman J. Haughey, Baltimore, MD (US); Ned Sacktor, Baltimore, MD (US)

(73) Assignees: Temple University—Of The Commonwealth System of Higher Education, Philadelphia, PA (US); The Johns Hopkins University, Baltimore, MD (US)

( * ) Notice: Subject to any disclaimer, the term of this patent is extended or adjusted under 35 U.S.C. 154(b) by 77 days.

(21) Appl. No.: 15/129,353

(22) PCT Filed: Mar. 24, 2015

(86) PCT No.: PCT/US2015/022201
§ 371 (c)(1),
(2) Date: Sep. 26, 2016

(87) PCT Pub. No.: WO2015/148475
PCT Pub. Date: Oct. 1, 2015

(65) Prior Publication Data
US 2017/0176408 A1    Jun. 22, 2017

Related U.S. Application Data

(60) Provisional application No. 61/969,620, filed on Mar. 24, 2014.

(51) Int. Cl.
*G01N 33/487* (2006.01)
*G01N 30/88* (2006.01)
*G01N 33/53* (2006.01)

(52) U.S. Cl.
CPC .......... *G01N 33/487* (2013.01); *G01N 30/88* (2013.01); *G01N 33/5308* (2013.01); *G01N 2030/8813* (2013.01); *G01N 2800/2814* (2013.01); *G01N 2800/52* (2013.01); *G01N 2800/56* (2013.01)

(58) Field of Classification Search
CPC .......... G01N 2800/26; G01N 2800/28; G01N 2800/2814
See application file for complete search history.

(56) References Cited

U.S. PATENT DOCUMENTS

| 7,972,807 B1 | 7/2011 | Phanstiel, IV et al. |
| 2003/0130357 A1 | 7/2003 | Ramesh et al. |
| 2012/0219970 A1 | 8/2012 | McGrath |

FOREIGN PATENT DOCUMENTS

WO    2012170998 A1    12/2012

OTHER PUBLICATIONS

Pegg, Anthony E. Spermidine/spermine-N1-acetyltransferase: a key metabolic regulator. Am J Physiol Endocrinol Metab 294: pp. E995-E1010. Mar. 18, 2008.
Perez-Leal, Oscar et al. Polyamine-Regulated Translation of Spermidine/Spermine-N1-Acetyltransferase. Molecular and Cellular Biology 0270-7306/12: pp. 1453-1467. Feb. 21, 2012.
Kramer, Debora L. et al. Polyamine Acetylation Modulates Polyamine Metabolic Flux, a Prelude to Broader Metabolic Consequences. Journal of Biological Chemistry vol. 283 No. 7, pp. 4241-4251. Dec. 18, 2007.
Zhang, Hui et al. Endogenous Reverse Transcription of Human Immunodeficiency Virus Type 1 in Physiological Microenvironments: an Important Stage for Viral Infection of Nondividing Cells. Journal of Virology, vol. 70, No. 5, pp. 2809-2824. May 1996.
Yoshizuka, Naoto et al. Human Immunodeficiency Virus Type 1 Vpr-Dependent Cell Cycle Arrest through a Mitogen-Activated Protein Kinase Signal Transduction Pathway. Journal of Virology, vol. 79, No. 17, pp. 11366-11381. Sep. 2005.
Borjabad, Alejandra et al. Gene Expression Profiles of HIV-1-Infected Glia and Brain: Toward Better Understanding of the Role of Astrocytes in HIV-1-Associated Neurocognitive Disorders. J Neuroimmune Pharmacol. 5(1): pp. 44-62. Mar. 2010.
Kaul, Marcus et al. Pathways to neuronal injury and apoptosis in HIV-associated dementia. Nature, vol. 410, pp. 988-994. Apr. 19, 2001.
Izmailova, Elena et al. HIV-1 Tat reprograms immature dendritic cells to express chemoattractants for activated T cells and macrophages. Nature Medicine, vol. 9, No. 2, pp. 191-197. Jan. 21, 2003.
Steiner, Mark-Steven et al. Chromogenic Sensing of Biogenic Amines Using a Chameleon Probe and the Red-Green-Blue Readout of Digital Camera Images. Analytical Chemistry, vol. 82, No. 20, pp. 8402-8405. Sep. 17, 2010.
Merali, Salim et al. Polyamine Analysis using N-hydroxysuccinimidyl-6-aminoquinoyl carbamate for pre-column derivatization. Journal of Chromatography B, 675, pp. 321-326. 1996.
Prendergast, Mark A. et al. Neurotoxic effects of the human immunodeficiency virus type-1 transcription factor Tat require function of a polyamine sensitive-site on the N-methyl-D-aspartate receptor. Brain Research 954, pp. 300-307. 2002.

*Primary Examiner* — Christopher Adam Hixson
(74) *Attorney, Agent, or Firm* — Riverside Law LLP

(57) ABSTRACT

Provided is a method of detecting mild neurocognitive disturbance (MNCD) or HIV associated dementia (HAD) in a patient comprising detecting the level of acetyl spermine and/or acetyl spermidine from a cerebrospinal fluid test sample of the patient; and comparing the level of acetyl spermine and/or acetyl spermidine in the test sample to the level of the acetyl spermine and/or acetyl spermidine in a cerebrospinal fluid control sample or to a control value for lack of neurocognitive impairment, MNCD or HAD; wherein an elevated level of acetyl spermine and/or acetyl spermidine in the test sample as compared to the level in the control sample or a control value for lack of neurocognitive impairment, or a level of acetyl spermine and/or acetyl spermidine that is similar to that of a control value for MNCD or HAD, indicates that the patient suffers from MNCD or HAD. Also provided are methods for measuring the progression of an HIV-1-associated neurocognitive disorder, as well as methods for staging such a disorder.

44 Claims, 8 Drawing Sheets

DETECTION OF HIV-1-ASSOCIATED NEUROCOGNITIVE DISORDERS

CROSS-REFERENCE TO RELATED APPLICATIONS

This application is the U.S. national phase application filed under 35 U.S.C. § 371 claiming benefit to International Patent Application No. PCT/US15/22201, filed Mar. 24, 2015, which is entitled to priority under 35 U.S.C. § 119(e) to U.S. Provisional Patent Application No. 61/969,620, filed Mar. 24, 2014, each of which application is hereby incorporated herein by reference in its entirety.

STATEMENT REGARDING FEDERALLY SPONSORED RESEARCH OR DEVELOPMENT

This invention was made with government support under P30MH092177 awarded by the National Institutes of Health (NIH). The government has certain rights in the invention.

BACKGROUND OF THE INVENTION

Soon after primary infection, HIV-1 is disseminated in the central nervous system (CNS) where productive replication in brain macrophages and microglia and limited expression of the viral genome in astrocytes may cause an array of toxic events that contribute to HIV-associated neurocognitive disorders (HAND) (Antinori A, et al., Neurology 2007; 69:1789-99). The presence of HIV-1 and expression of viral proteins, even at low levels, in the brains of HIV patients taking combined antiretroviral therapy (cART) is often associated with neurocognitive disorders. It is estimated that greater than 50% of HIV-1 infected individuals with low viral load and high CD4 lymphocyte cell counts, exhibit some form of HAND, and it is suggested that cART may be at least partially responsible for these impairments (Price R W, et al., The Journal of infectious diseases 2008; 197 Suppl 3:S294-306). Based on the severity of disease, HAND is divided into three classes: asymptomatic neurocognitive impairment (ANI), mild cognitive and motor disorders (MCMD), and HIV-1 associated dementia (HAD) (Gannon P, et al., Current opinion in neurology 2011; 24:275-83 and Woods S P, et al., Neuropsychology review 2009; 19:152-68). Some HIV patients however, have no cognitive impairment (NCI). At present, there are no molecular diagnostic biomarkers for different classes of HAND and diagnosis is mostly based on exclusion of other possible causes accompanied by neurological exam, neuropsychological tests, and brain MRI scan. Pathologically, HIV-1 infection usually impacts cortical and subcortical regions and in the case of HIV encephalitis (HIVE) neuronal loss, astrogliosis, infiltrating macrophages, microglial nodules and multinucleated giant cells may be observed (Desplats P, et al., Neurology 2013; 80:1415-23 and Masliah E, et al., Aids 2000; 14:69-74).

At subcellular levels, HIV-1-associated neuronal injury occurs indirectly by a neurotoxic environment created by products of virally infected macrophage/microglia such as chemokines, cytokines, and viral proteins including gp120, Tat and others. Communication between viral proteins and the host, through a variety of signaling receptors including TNFα, NMDA, AMPA and others perturb the homeostasis of neuronal cells leading to their injury and death (Gelman B B, Soukup V M, Schuenke K W, et al. Acquired neuronal channelopathies in HIV-associated dementia. Journal of neuroimmunology 2004; 157:111-9 and Kaul M, et al., Nature 2001; 410:988-94). Endogenous polyamines (putrescine, spermidine, and spermine) are known for modulating NMDA receptor function and early studies demonstrated that HIV-1 Tat-induced neurotoxicity involves the interaction between polyamines and NMDA receptors (Prendergast M A, et al., Brain research 2002; 954:300-7). Besides the effect on neurons, the polyamines, especially spermine, enhance astrocyte coupling through gap junctions (Benedikt J, et al., Neuroreport 2012; 23:1021-5). Importantly, spermine accumulates almost exclusively in glial cells but not in neurons (Laube G, et al., The Journal of comparative neurology 2002; 444:369-86 and Laube G, et al., Glia 1997; 19:171-9). Therefore, these polyamines likely play a central role in astrocyte function.

Intracellular levels of polyamines are tightly regulated by homeostatic interactions between the anabolic and catabolic components of their metabolism. Spermidine/spermine-$N^1$-acetytransferase (SSAT) is the key enzyme in the catabolism of polyamines. It catalyzes the transfer of acetyl groups from acetyl-CoA onto the intracellular polyamines, spermidine or spermine. Acetylation reduces the positive charges on these molecules, alters their binding activity and renders them susceptible to cellular excretion and/or catabolism (Pegg A E, Am J Physiol Endocrinol Metab 2008; 294:E995-1010). Importantly, acetylation also alters their ability to activate homeostatic responses. In mammalian cells, SSAT is tightly regulated and is highly inducible by polyamines (Fogel-Petrovic M, et al., Biochemistry 1996; 35:14436-44). The importance of SSAT in regulating polyamine homeostasis is indicated by its very short half-life, which is on the order of 20 min; this allows the cell to rapidly change enzyme and polyamine levels (McCloskey D E, et al., J Biol Chem 2003; 278:13881-7). SSAT levels can also be induced by a variety of other stimuli including HIV-1 Tat. These increases in SSAT are regulated by translational control mechanisms (Perez-Leal O, et al., Mol Cell Biol 2012; 32:1453-67 and Perez-Leal 0, et al., Amino acids 2012; 42:611-7).

Recently, the ability of SSAT to control polyamine flux through the metabolic pathway was elucidated by showing that the overexpression of SSAT leads to futile metabolic cycling (Kramer D L, et al., J Biol Chem 2008; 283:4241-51). However, the existence of this polyamine cycle and its consequences in patients with HAND has not been determined.

There remains a need for a dependable means of detecting HIV-1-associated neurocognitive disorders, and for monitoring the progress of individuals afflicted with such disorders. The present invention fulfills this need.

SUMMARY OF THE INVENTION

The invention provides a method of detecting mild neurocognitive disturbance (MNCD) or HIV associated dementia (HAD) in a patient. In one embodiment, the method comprises (a) detecting the level of acetyl spermine and/or acetyl spermidine from a biological test sample of the patient; and (b)(i) comparing the level of acetyl spermine and/or acetyl spermidine in the test sample to the level of acetyl spermine and/or acetyl spermidine in a biological control sample; wherein an elevated level of acetyl spermine and/or acetyl spermidine in the test sample as compared to the level in the control sample indicates that the patient suffers from mild neurocognitive disturbance or HIV associated dementia; or (b)(ii) comparing the level of acetyl spermine and/or acetyl spermidine in the test sample to a standard value or standard value range for mild neurocognitive disturbance or HIV associated dementia; wherein a level of acetyl spermine and/or acetyl spermidine that is similar to that of the standard value or that fits within the standard value range for mild neurocognitive disturbance or HIV associated dementia indicates that the patient suffers from mild neurocognitive disturbance or HIV associated dementia.

In one embodiment, the acetyl spermine and/or the acetyl spermidine level is detected by HPLC, mass spectroscopy or chromogenic sensing.

In one embodiment, the acetyl spermine and/or the acetyl spermidine is derivatized prior to being detected.

In one embodiment, the control sample is from a healthy subject without neurocognitive impairment or an HIV-1-infected subject without neurocognitive impairment.

In one embodiment, mild neurocognitivedisturbance is detected.

In one embodiment, HIV associated dementia is detected.

In one embodiment, a level of the acetyl spermidine in the test sample that is from about 1.5-fold to about 2.5-fold that of the control sample indicates that the patient suffers from mild neurocognitive disturbance.

In one embodiment, a level of the acetyl spermidine in the test sample that is greater than about 2.6-fold that of the control sample indicates that the patient suffers from HIV-1-associated neurocognitive disorder.

In one embodiment, a level of the acetyl spermine in the test sample that is from about 3.0-fold to about 4.5-fold that of the control sample indicates that the patient suffers from mild neurocognitive disturbance.

In one embodiment, a level of the acetyl spermine in the test sample that is greater than about 4.6-fold that of the control sample indicates that the patient suffers from HIV associated dementia.

In one embodiment, a sum of the levels of the acetyl spermidine and the acetyl spermine in the test sample that is from about 2.5-fold to about 4.0-fold that of the control sample indicates that the patient suffers from mild neurocognitive disturbance.

In one embodiment, a sum of the levels of the acetyl spermidine and the acetyl spermine in the test sample that is greater than about 4.1-fold that of the control sample indicates that the patient suffers from HIV associated dementia.

In one embodiment, the control value for lack of neurocognitive impairment is 1.3 nmol/ml CSF for acetyl spermine, 1.8 nmol/ml CSF for acetyl spermidine or 3.1 nmol/ml CSF for the sum of acetyl spermidine and acetyl spermine.

In one embodiment, the acetyl spermine standard value for mild neurocognitive disturbance is from about 4.2 nmol/ml to about 6.0 nmol/ml CSF.

In one embodiment, the acetyl spermine control standard for HIV associated dementia is at least about 6.2 nmol/ml CSF.

In one embodiment, the acetyl spermidine standard for mild neurocognitive disturbance is from about 3.0 nmol/ml to about 4.0 nmol/ml CSF.

In one embodiment, the acetyl spermidine standard value for HIV associated dementia is at least about 5.0 nmol/ml CSF.

In one embodiment, the standard value for the sum of acetyl spermidine and acetyl spermine for mild neurocognitive disturbance is from about 7.2 nmol/ml to about 10.0 nmol/ml CSF.

In one embodiment, the standard value for the sum of acetyl spermidine and acetyl spermine for HIV associated dementia is at least about 11.2 nmol/ml CSF.

In one embodiment, the patient is female.

The invention also provides a method for monitoring the progression or improvement of an HIV-1-associated neurocognitive disorder (HAND) in a patient. In one embodiment, the method comprises measuring the level of acetyl spermine and/or acetyl spermidine from a first cerebrospinal fluid test sample of the patient at a first time point; and measuring the level of acetyl spermine and/or acetyl spermidine from a second cerebrospinal fluid test sample of the patient at a second time point; wherein an elevated level of acetyl spermine and/or acetyl spermidine in the second test sample compared to the level of acetyl spermine or acetyl spermidine in the first test sample indicates that the HIV-1-associated neurocognitive disorder in the patient has progressed; wherein a lower level of the acetyl spermine and/or acetyl spermidine in the second test sample compared to the level of acetyl spermine or acetyl spermidine in the first test sample indicates that the HIV-1-associated neurocognitive disorder in the patient has improved; and wherein an unchanged level of the acetyl spermine and/or acetyl spermidine in the second test sample compared to the level of acetyl spermine or acetyl spermidine in the first test sample indicates that the HIV-1-associated neurocognitive disorder in the patient has not changed.

In one embodiment, the acetyl spermine and/or the acetyl spermidine is detected by HPLC, mass spectroscopy or chromogenic sensing.

In one embodiment, the acetyl spermine and/or the acetyl spermidine is derivatized prior to being detected.

In one embodiment, the HIV-1-associated neurocognitive disorder is mild neurocognitive disturbance.

In one embodiment, the HIV-1-associated neurocognitive disorder is HIV associated dementia.

In one embodiment, the patient is female.

The invention also provides a method for staging an HIV-1-associated neurocognitive disorder (HAND) in an HIV patient. In one embodiment, the method comprises measuring the level of acetyl spermine and/or acetyl spermidine in a cerebrospinal fluid test sample of a patient; and comparing the level of acetyl spermine and/or acetyl spermidine to the level of acetyl spermine and/or acetyl spermidine in a sample of a control person without the HIV-1-associated neurocognitive disorder, a control from a person with a certain known stage of progression of the HIV-1-associated neurocognitive disorder, or to a series of standard values indicative of the stages; determining which control sample or control standard has the most similar level of acetyl spermine or acetyl spermidine to that of the patient; and assigning to the patient the stage of the control sample or standard value with the most similar level of acetyl spermine or acetyl spermidine to that of the patient.

In one embodiment, the acetyl spermine and/or the acetyl spermidine is detected by HPLC, mass spectroscopy or chromogenic sensing.

In one embodiment, the acetyl spermine and/or the acetyl spermidine is derivatized prior to being detected.

In one embodiment, the HIV-1-associated neurocognitive disorder is mild neurocognitive disturbance or HIV associated dementia.

In one embodiment, the certain known stage of progression of the HIV-1-associated neurocognitive disorder is mild neurocognitive disturbance or HIV associated dementia.

In one embodiment, the patient is female.

The invention provides a method of detecting asymptomatic neurocognitive impairment (ANI) in a patient. In one embodiment, the method comprises detecting the level of acetyl spermidine from a cerebrospinal fluid test sample of the patient; comparing the level of acetyl spermidine in the test sample to the level of acetyl spermidine in a control sample or to a standard value for acetyl spermidine; wherein an elevated level of acetyl spermidine in the test sample as compared to the level in the control sample or a level of acetyl spermidine that is similar to that of the standard value indicates that the patient suffers from asymptomatic neurocognitive impairment.

In one embodiment, the acetyl spermidine is detected by HPLC, mass spectroscopy or chromogenic sensing.

In one embodiment, the acetyl spermidine is derivatized prior to being detected.

In one embodiment, the control sample is from a healthy subject without neurocognitive impairment or an HIV-1-infected subject without neurocognitive impairment.

In one embodiment, the level of the acetyl spermidine in the test sample that is from about 1.5-fold to about 2.5-fold that of the control sample indicates that the patient suffers from asymptomatic neurocognitive impairment.

In one embodiment, the standard value for lack of neurocognitive impairment is about 1.5 nmol/ml of cerebrospinal fluid.

In one embodiment, the standard value for asymptomatic neurocognitive impairment is from about 2.5 nmol/ml to about 3 nmol/ml of cerebrospinal fluid.

In one embodiment, the patient is female.

The invention also provides a method of diagnosing different severities of HIV-associated neurocognitive disorders in a patient, the method comprising detecting an enhanced level of acetylated polyamine in the patient compared to the level of acetylated polyamine in a comparator control.

In one embodiment, the different severities of HIV-associated neurocognitive disorders is selected from the group consisting of asymptomatic neurocognitive impairment (ANI), mild cognitive and motor disorders (MCMD), and HIV-1 associated dementia (HAD).

In one embodiment, the acetylated polyamine is selected from the group consisting of acetyl spermine, acetyl spermidine, any a combination thereof.

In one embodiment, acetylated polyamine is detected in a biological sample isolated from the patient.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 5, comprising FIG. 5A) SSAT activity is elevated in the lysates from the brains of patients with HAND. A Kruskal-Wallis test was used to compare the groups. The mean differential between SSAT activity in the brain of MCMD as compared to No-HIV or HIV but No-NCI in pmol/mg protein/hr is (mean±SD) 35.80±2.972, 12.50±1.25, 18.30±0.985, respectively. FIG. 5B) Acetylspermidine levels are elevated in the lysates from the brains of patients with HAND. A Kruskal-Wallis test was used to compare the groups. The mean differential between acetylspermidine levels in the brain of MCMD as compared to No-HIV or HIV but No-NCI in pmol/mg protein is (mean±SD) 60.00±5.57, 4.27±0.86, 1.56±0.12, respectively.

FIG. 6, comprising FIG. 6A) SSAT activity in human primary astrocytes transduced to express HIV-1 Tat. A one-way ANOVA with Tukey-Kramer test was used to compare the groups. The mean differential between SSAT activity in the astrocytes transduced with HIV-Tat as compared to untransduced or transduced with Adeno-null in pmol/mg protein/hr are 27.93±2.71, 12.03±1.36, 12.03±1.60, respectively ($p<0.0001$). FIG. 6B) Acetyl-CoA pools in primary astrocytes expressing HIV-1 Tat. A one-way ANOVA with Tukey-Kramer test was used to compare the groups. As consequence of polyamine flux, the acetyl-CoA levels are decreased in astrocytes expressing HIV-1 Tat as compared to empty plasmid controls ($p>0.0001$).

DETAILED DESCRIPTION OF THE INVENTION

Figure 1:
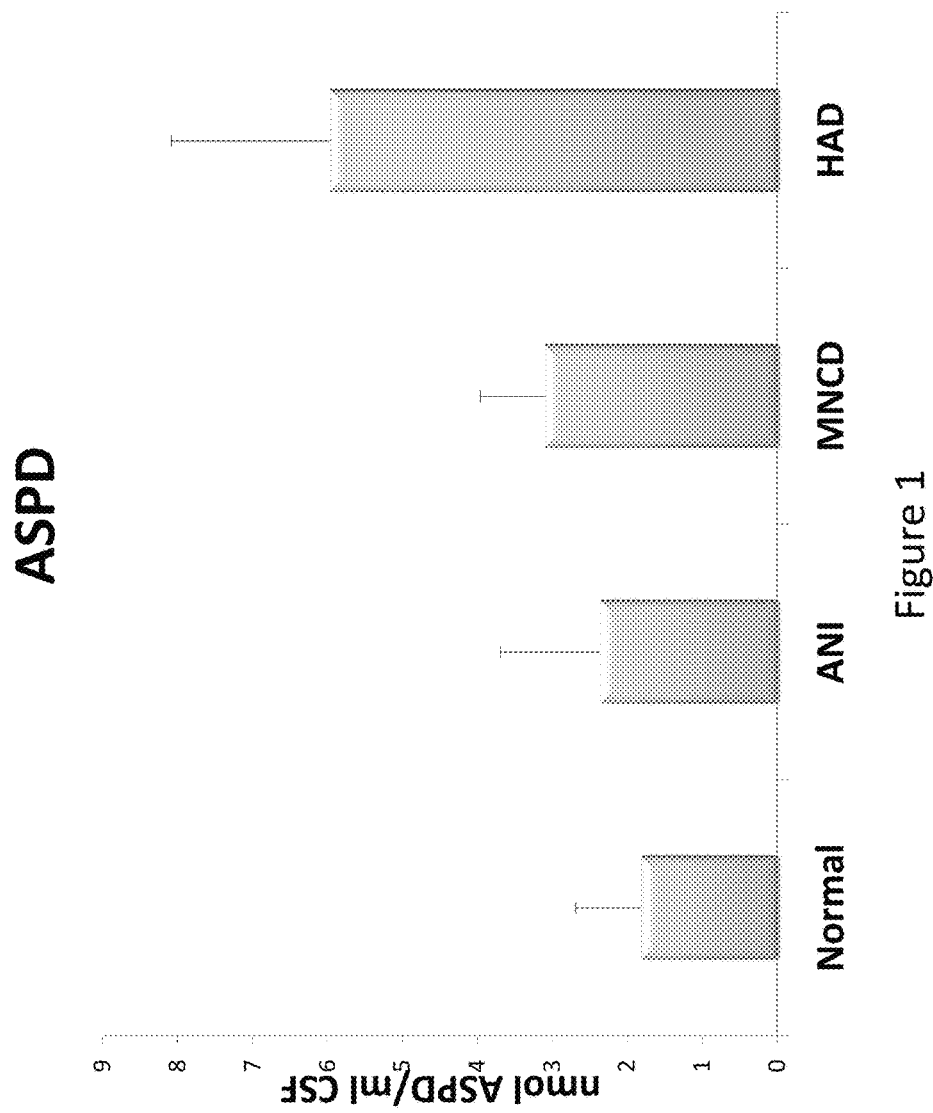
FIG. 1 illustrates the acetyl spermidine (ASPD) levels in CSF from 10 ANI, 9 MNCD and 11 HAD subjects as compared to 10 HIV-infected control subjects with normal cognition. The averages are shown. The error bars represent the standard deviation.

Neuro-AIDS encompasses a wide range of HIV-1 associated neurocognitive disorders (HAND) including asymptomatic neurocognitive impairment (ANI), mild neuro-cognitive disturbance (MNCD) and HIV associated dementia (HAD). Currently there are no early biomarkers for HIV-1-associated neurocognitive disorders. The present invention meets the need for the detection of HIV-1-associated neurocognitive disorders.

Provided are methods for detecting an HIV-1-associated neurocognitive disorder in a patient comprising detecting the level of acetyl spermine or acetyl spermidine from a CSF test sample of the patient; and comparing the level of acetyl spermine or acetyl spermidine in the test sample to the level of the acetyl spermine or acetyl spermidine in a control sample (or and comparing the level of acetyl spermine or acetyl spermidine to a control value); wherein an elevated level of acetyl spermine or acetyl spermidine in the test sample as compared to the level in the control sample (or to the control value) indicates that the patient suffers from an HIV-1-associated neurocognitive disorder. Also provided are methods for measuring the progression of an HIV-1-associated neurocognitive disorder, as well as methods for staging such a disorder.

The methods of the present invention may be used to supplement typical methods of diagnosing HIV-1-associated neurocognitive disorders. HIV-1-associated neurological disorders are typically diagnosed by employing neuropsychological testing (McArthur et al., 2004, *Arch Neurol* 61: 1687-1696), and may also be detected by magnetic resonance spectroscopy studies (Mohamed et al., 2010, *Magn Reson Imaging* 28(9):1251-1257).

The methods of the present invention may be used on subjects irrespective of whether they are being treated with antiretroviral therapy or not. The antiretroviral therapy may be a combination antiretroviral therapy or not.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting. The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "biomarker" is a characteristic that is objectively measured and evaluated as an indicator of normal biological processes, pathological processes, or pharmacological responses to a therapeutic intervention. The biomarker can for example describe a substance whose detection indicates a particular disease state. The biomarker may be a peptide that causes disease or is associated with susceptibility to disease. In some instances, the biomarker may be a gene that causes disease or is associated with susceptibility to disease. In other instances, the biomarker is a metabolite. In any event, the biomarker can be differentially present (i.e., increased or decreased) in a biological sample from a subject or a group of subjects having a first phenotype (e.g., having a disease) as compared to a biological sample from a subject or group of subjects having a second phenotype (e.g., not having the disease). A biomarker is preferably differentially present at a level that is statistically significant (i.e., a p-value less than 0.05 and/or a q-value of less than 0.10 as determined using either Welch's T-test or Wilcoxon's rank-sum Test).

The term "body fluids" includes any fluids which can be obtained from a mammalian body. Thus, the term "body fluids" also includes homogenates of any tissues and other body matter. More particularly, however, the term "body fluids" includes fluids that are normally or abnormally secreted by or excreted from the body. The respective fluids may include, but are not limited to: blood, plasma, lymph, urine, and cerebrospinal fluid, blood, plasma, and cerebrospinal fluid.

The phrase "biological sample" is used herein in its broadest sense. A sample may be of any biological tissue or fluid from which biomarkers of the present invention may be assayed. Examples of such samples include but are not limited to blood, lymph, urine, gynecological fluids, biopsies, amniotic fluid and smears. Samples that are liquid in nature are referred to herein as "bodily fluids." Body samples may be obtained from a patient by a variety of techniques including, for example, by scraping or swabbing an area or by using a needle to aspirate bodily fluids. Methods for collecting various body samples are well known in the art. Frequently, a sample will be a "clinical sample," i.e., a sample derived from a patient. Such samples include, but are not limited to, bodily fluids which may or may not contain cells, e.g., blood (e.g., whole blood, serum or plasma), urine, saliva, tissue or fine needle biopsy samples, and archival samples with known diagnosis, treatment and/or outcome history. Biological or body samples may also include sections of tissues such as frozen sections taken for histological purposes. The sample also encompasses any material derived by processing a biological or body sample. Derived materials include, but are not limited to, cells (or their progeny) isolated from the sample, proteins or nucleic acid molecules extracted from the sample. Processing of a biological or body sample may involve one or more of: filtration, distillation, extraction, concentration, inactivation of interfering components, addition of reagents, and the like.

"Sample" or "biological sample" as used herein means a biological material isolated from a subject. The biological sample may contain any biological material suitable for detecting the desired biomarkers, and may comprise cellular and/or non-cellular material from the subject. The sample can be isolated from any suitable biological tissue or fluid such as, for example, blood, blood plasma, urine, or cerebral spinal fluid (CSF).

The term "comparator control,", as used herein, relates to a level of expression or activity which may be determined at the same time as the test sample by using a sample previously collected and stored from a subject whose disease state, e.g. cancerous, non-cancerous, is/are known.

As used herein, the term "control sample" refers to a CSF sample taken from: (i) a healthy subject without neurocognitive impairment or (ii) an HIV-1-infected subject without neurocognitive impairment. In some embodiments the total acetyl polyamine level is the level of acetyl spermine and the level of acetyl spermidine combined.

As used herein, the term "HIV-1-associated neurocognitive disorder" also known as "neuroAIDS" refers to a wide range of neurological abnormalities that are associated with HIV-I infection, including asymptomatic neurocognitive impairment (ANI), mild neuro-cognitive disturbance (MNCD) and HIV associated dementia (HAD).

The terms "marker" and "epigenetic marker" used herein refer to a distinguishing or characteristic substance that may be found in a biological material. The substance may, for example, be a protein, an enzyme, an RNA molecule or a DNA molecule. Non-limiting examples of such a substance include a kinase, a methylase, and an acetylase. The terms also refer to a specific characteristic of the substance, such as, but not limited to, a specific phosphorylation, methylation, or acetylation event or pattern, making the substance distinguishable from otherwise identical substances. The terms further refer to a specific modification, event or step occurring in a signaling pathway or signaling cascade, such as, but not limited to, the deposition or removal of a specific phosphate, methyl, or acetyl group.

"Measuring" or "measurement," or alternatively "detecting" or "detection," or alternatively "determine" or "determining" means assessing the presence, absence, quantity or amount of either a given substance within a clinical or subject-derived sample, including the derivation of qualitative or quantitative concentration levels of such substances.

As used herein, "phenotypically distinct" is used to describe organisms, tissues, cells or components thereof, which can be distinguished by one or more characteristics, observable and/or detectable by current technologies. Each of such characteristics may also be defined as a parameter contributing to the definition of the phenotype. Wherein a phenotype is defined by one or more parameters an organism that does not conform to one or more of the parameters shall be defined to be distinct or distinguishable from organisms of the phenotype.

The term "polyamine" herein refers to a straight-chain aliphatic hydrocarbon having two or more primary amino groups. Known biogenic polyamines may include, but are not limited to, putrescine, cadaverine, spermidine, spermine, 1,3-diaminopropane, caldine, homospermidine, 3-aminopropylcadaverine, norspermine, thermospermine, caldopentamine. Preferred polyamines in accordance with an aspect of the present invention may be putrescine, spermidine and spermine.

The terms "subject," "patient," "individual," and the like are used interchangeably herein, and refer to any animal, or cells thereof whether in vitro or in situ, amenable to the methods described herein. In certain non-limiting embodiments, the patient, subject or individual is a human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are culture in vitro. In other embodiments, the cells are not cultured in vitro.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

As used herein, the term "standard value" refers to an acetyl spermine, acetyl spermidine, or total acetylated polyamine level that indicates that the patient suffers from mild neurocognitive disturbance or that the patient suffers from HIV associated dementia. A standard value for lack of neurocognitive impairment may be an acetyl spermine level that is about 1.3 nmol/ml CSF, an acetyl spermidine level that is about 1.8 nmol/ml CSF or a total acetylated polyamine level that is about 3.1 nmol/ml. The standard value for MNCD may be an acetyl spermine level that is from about 4.2 nmol/ml CSF to about 6.0 nmol/ml CSF, an acetyl spermidine level that is from about about 3.0 nmol/ml CSF to about 4.0 nmol/ml CSF or a total acetylated polyamine level that is from about 7.2 nmol/ml to about 10.0 nmol/ml CSF. The standard value for HAD may be an acetyl spermine level that is at least about 6.2 pmol/ml CSF, an acetyl spermidine level that is at least about 5 nmol/ml CSF or a total acetylated polyamine level that is at least 11.2 nmol/ml CSF. In preferred embodiments, the standard values are based on levels of acetyl spermine and/or acetyl spermidine that are measured in raw CSF.

If the CSF test or control sample is diluted or concentrated before detection of acetyl spermine and/or acetyl spermidine, then the necessary adjustments must be made to normalize the results in the test or control sample to those in raw CSF.

As used herein, the term "control from a person with a certain known stage of progression of the HIV-I-associated neurocognitive disorder" refers to a sample taken from a subject suffering from a certain, identifiable, stage of progression of the HIV-I-associated neurocognitive disorder. In some embodiments, the HIV-I-associated neurocognitive disorder is MNCD or HAD.

The term to "treat," as used herein, means reducing the frequency with which symptoms are experienced by an individual or subject or administering an agent or compound to reduce the frequency with which symptoms are experienced. In some instances, "treat" and "treating" are not limited to the case where the subject (e.g. patient) is cured and the disease is eradicated. Rather, the present invention also contemplates treatment that merely reduces symptoms, improves (to some degree) and/or delays disease progression. The term "treatment" also refers to the alleviation, amelioration, and/or stabilization of symptoms, as well as delay in progression of symptoms of a particular disorder.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates to the identification of biomarkers that are associated with HIV-1 associated neurocognitive disorders (HAND). HIV-1-associated neurocognitive disorders, also known as neuroAIDS, are characterized by a wide range of neurological abnormalities comprising, but not limited to, ANI, MNCD and HAD.

Such biomarkers could be used for HAND screening and diagnosis, as well as potentially for assessing response to new therapies. In one embodiment, the biomarkers of the invention allow a more accurate diagnosis or prognosis of HAND. In one embodiment, the biomarkers of the invention allow the monitoring of HAND, such that a comparison of biomarker levels allows an evaluation of disease progression in subjects that have been diagnosed with HAND, or that do not yet show any clinical signs of HAND. Moreover, the biomarkers of the invention may be used in concert with known biomarkers such that a more accurate diagnosis or prognosis of HAND may be made.

The biomarkers disclosed herein may be used in combination with existing clinical diagnostic measures of HAND. Combinations with clinical diagnostics may facilitate the disclosed methods, or confirm results of the disclosed methods (for example, facilitating or confirming diagnosis, monitoring progression or regression, and/or determining predisposition to HAND).

Generally, any suitable method may be used to analyze the biological sample in order to determine the level(s) of the one or more biomarkers in the sample. Suitable methods include those disclosed in the Examples section as well as chromatography (e.g., HPLC, gas chromatography, liquid chromatography), mass spectrometry (e.g., MS, MS-MS), enzyme-linked immunosorbent assay (ELISA), antibody linkage, other immunochemical techniques, and combinations thereof. Further, the level(s) of the one or more biomarkers may be measured indirectly, for example, by using an assay that measures the level of a compound (or compounds) that correlates with the level of the biomarker(s) that are desired to be measured.

The biomarkers of the invention can be used to facilitate the optimum selection of treatment protocols, and open new venues for the development of effective therapy for HAND. Biomarkers of the invention can be used to guide treatment selection for individual patients, as well as to guide the development of new therapies specific to each type of HAND.

Provided herein are methods for assessing cognitive function, assessing cognitive impairment, diagnosing or aiding diagnosis of cognitive impairment by obtaining measured levels of one or more biomarkers of the invention in a biological sample from an individual, such as for example, a CSF sample from an individual, and comparing those measured levels to reference levels.

The levels of the biomarkers of the invention may be assessed in several different biological samples, for example bodily fluids. Non-limiting examples of bodily fluid include whole blood, plasma, serum, bile, lymph, pleural fluid, semen, saliva, sweat, urine, and CSF.

The bodily fluid is obtained from the individual using conventional methods in the art. For instance, one skilled in the art knows how to draw blood and how to process it in order to obtain serum and/or plasma for use in the method. Generally speaking, the method preferably maintains the integrity of the biomarkers of the invention such that it can be accurately quantified in the bodily fluid.

Detection of Acetyl Spermine and/or Acetyl Spermidine

The methods described herein rely on assessing the level of acetyl spermine and/or acetyl spermidine, whose level correlates in a statistically significant manner with the diagnosis and staging of HIV-1-associated neurocognitive disorders, in a CSF sample obtained from a patient. The sample is obtained from the subject using conventional methods in the art. For instance, one skilled in the art knows how to draw CSF and how to process it in order to use it in practicing the described methods. Generally speaking, the method of obtaining and storing, if necessary, the sample preferably maintains the integrity of one or both acetyl spermine and acetyl spermidine such that it can be accurately quantified in the test sample.

The methods of the invention include quantitatively measuring the level of one or both acetyl spermine and acetyl spermidine. Methods of quantitatively assessing the level of acetyl spermine and/or acetyl spermidine in a biological fluid are well known in the art. Methods of quantitatively assessing the level of acetyl spermine and/or acetyl spermidine comprise, for example, high-performance liquid chromatography (HPLC), mass spectroscopy (e.g., MS, MSMS) or chromogenic methods such as those described in Steiner et al., 2010, *Anal. Chem.* 82:8402-8405. A variety of methods for HPLC analysis of acetyl spermine or acetyl spermidine are available and most involve a pre-column derivatization of the amino groups of the these polyamines. In preferred embodiments, N-hydroxysuccinimidyl-6-aminoquinoyl carbamate (AccQ.Fluor) is used as a polyamine pre-column derivatization reagent prior to HPLC analysis using a 5-µg $C_8$ reversed-phase column. (Merali S, Clarkson, A. B. Jr., 1996, *J of Chromatography* 675:321-326). Any reverse phase HPLC column may be used for quantifying acetyl spermine and/or acetyl spermidine, and a person of skill in the art would understand how to adjust the solvent column gradient accordingly.

In some embodiments, an amine-reactive probe such as Py-1 (available as Chromeo™ P503 from Active Motif Chromeon, Tegernheim, Germany) is used to bind acetyl spermine and/or acetyl spermidine to aid in their detection. Py-1 is blue and virtually nonfluorescent in its nonconjugated form but shows a strong increase in fluorescence intensity when covalently reacted with primary amino groups.

The control sample may comprise a CSF sample taken from: (i) a healthy subject without neurocognitive impairment or (ii) an HIV-1-infected subject without neurocognitive impairment. In some embodiments the total acetyl polyamine level is the level of acetyl spermine and the level of acetyl spermidine combined. The control may be an individual sample or may be pooled from several individuals.

A standard value for lack of neurocognitive impairment may be an acetyl spermine level that is about 1.3 nmol/ml CSF, an acetyl spermidine level that is about 1.8 nmol/ml CSF or a total acetylated polyamine level that is about 3.1 nmol/ml. The standard value for MNCD may be an acetyl spermine level that is from about 4.2 nmol/ml CSF to about 6.0 nmol/ml CSF, an acetyl spermidine level that is from about about 3.0 nmol/ml CSF to about 4.0 nmol/ml CSF or a total acetylated polyamine level that is from about 7.2 nmol/ml to about 10.0 nmol/ml CSF. The standard value for HAD may be an acetyl spermine level that is at least about 6.2 pmol/ml CSF, an acetyl spermidine level that is at least about 5.0 nmol/ml CSF or a total acetylated polyamine level that is at least about 11.2 nmol/ml CSF. In preferred embodiments, the standard values are based on levels of acetyl spermine and/or acetyl spermidine that are measured in raw CSF.

If the CSF test or control sample is diluted or concentrated before detection of acetyl spermine and/or acetyl spermidine, then the necessary adjustments must be made to normalize the results in the test or control sample to those in raw CSF. In some embodiments, the CSF is boiled for deproteinization prior to measuring the levels of acetyl spermine and/or acetyl spermidine.

Disease Progression Monitoring

In another embodiment, the invention provides a method of monitoring the progression of an HIV-1-associated neurocognitive disorder in a subject. CSF samples are obtained from the subject at different time points and analyzed as described above. An elevated level of acetyl spermine or acetyl spermidine in a later sample relative to an earlier sample is an indication that the HIV-1-associated neurocognitive disorder has progressed, i.e., the neurocognitive disorder has become more serious. A lower level of acetyl spermine or acetyl spermidine in a later sample relative to an earlier sample is an indication that the HIV-1-associated neurocognitive disorder has improved, i.e., the neurocognitive disorder has become less serious.

In another embodiment, the invention provides methods for determining the course of an HIV-1-associated neurocognitive disorder in a subject. Disease course refers to changes in disease status over time, including disease progression (worsening) and disease regression (improvement). Over time, the amounts or relative amounts (e.g., the pattern) of the biomarkers changes. For example, levels of various biomarkers of the present invention increase with progression of disease. Accordingly, this method involves measuring the level of one or more biomarkers in an individual at two or more different time points, e.g., a first time and a second time, and comparing the change in amounts. The course of disease is determined based on these comparisons.

In some instances, the levels of various biomarkers of the invention decreases with disease progression. In this method, the level of one or more biomarkers in a sample from an individual is measured at two or more different time points, e.g., a first time and a second time, and the change in levels, if any is assessed. The course of disease is determined based on these comparisons.

Similarly, changes in the rate of disease progression (or regression) may be monitored by measuring the level of one or more biomarkers at different times and calculating the rate of change in biomarker levels. The ability to measure disease state or rate of disease progression is important for drug treatment studies where the goal is to slow down or arrest disease progression using therapy.

Additional embodiments of the invention relate to the communication of the results or diagnoses or both to technicians, physicians or patients, for example. In certain embodiments, computers are used to communicate results or diagnoses or both to interested parties, e.g., physicians and their patients.

In certain embodiments, the methods of the invention further comprise managing individual treatment based on their disease status. Such management includes the actions of the physician or clinician subsequent to determining an HIV-1-associated neurocognitive disorder status. For example, if a physician makes a diagnosis of an HIV-1-associated neurocognitive disorder, then a certain regime of treatment, such as prescription or administration of the therapeutic compound might follow. Alternatively, a diagnosis of a non-HIV-1-associated neurocognitive disorder in a subject might be followed by further testing to determine any other diseases that might the patient might be suffering from. Also, if the test is inconclusive with respect to an HIV-1-associated neurocognitive disorder in a subject status, further tests may be called for.

In a preferred embodiment of the invention, a diagnosis based on the presence or absence or relative levels in the biological sample of an individual of the relevant biomarkers disclosed herein is communicated to the individual as soon as possible after the diagnosis is obtained.

According to yet another aspect, the present invention provides a method of assessing efficacy of a treatment of an HIV-1-associated neurocognitive disorder in a subject comprising: a) determining a baseline level of biomarkers in a first sample obtained from the subject before receiving the treatment; b) determining the level of same biomarkers in a second sample obtained from the subject after receiving the treatment; wherein an alteration in the levels of the biomarkers in the post-treatment sample is correlated with a positive treatment outcome.

Disease Staging

In another embodiment, the invention provides a method of staging the HIV-1-associated neurocognitive disorder in a subject. The level of acetyl spermine and/or acetyl spermidine is measured in a CSF test sample of a patient. The level of acetyl spermine and/or acetyl spermidine in the CSF test sample is compared to the level of acetyl spermine and/or acetyl spermidine in a CSF sample of a control person without the HIV-1-associated neurocognitive disorder or a control from a person with a certain known stage of progression of said HIV-1-associated neurocognitive disorder or a series of standard values known to be indicative of that stage. Which control or standard value has the most similar level of the acetylated polyamine(s) to that of the patient is determined. The stage of the control or standard value with the most similar level of the acetylated polyamine to that of the patient is assigned to the patient.

In yet another embodiment, the invention provides methods for determining the stage of HIV-1-associated neurocognitive disorder in a subject. Each stage of the disorder can be characterized by the amount of a biomarker or relative amounts of a set of biomarkers (i.e., a pattern) that are found in a sample obtained from the subject. The stage of HIV-1-associated neurocognitive disorder in a subject is determined by measuring the relevant biomarker or biomarkers and then either submitting them to a classification algorithm or comparing them with a reference amount and/or pattern of biomarkers that is associated with the particular stage.

Kits

A kit is envisaged for every method disclosed. The following description of a kit useful for diagnosing an HIV-1-associated neurocognitive disorder in an individual by measuring the level of a biomarker in a biological sample therefore is not intended to be limiting and should not be construed that way.

The kit may comprise a negative control containing a biomarker at a concentration of about the concentration of the biomarker which is present in a biological sample of an individual who does not have an HIV-1-associated neurocognitive disorder or does not have increased risk for an HIV-1-associated neurocognitive disorder. The kit may also include a positive control containing the biomarker at a concentration of about the concentration of the biomarker which is present in a biological sample of an individual who as an HIV-1-associated neurocognitive disorder or has increased risk for an HIV-1-associated neurocognitive disorder.

The kit of the invention can be used to assess the status of an HIV-1-associated neurocognitive disorder in an individual, e.g., to diagnose an HIV-1-associated neurocognitive disorder or to assess the degree of an HIV-1-associated neurocognitive disorder in the individual. The phrase "HIV-1-associated neurocognitive disorder status" includes any distinguishable manifestation of the disease, including non-HIV-1-associated neurocognitive disorder disease, e.g., normal. For example, disease status includes, without limitation, the presence or absence of an HIV-1-associated neurocognitive disorder (e.g., an HIV-1-associated neurocognitive disorder vs. non-HIV-1-associated neurocognitive disorder), the risk of developing disease, the stage of the disease, the progress of disease (e.g., progress of disease or remission of disease over time) and the effectiveness or response to treatment of disease. Based on this status, further procedures may be indicated, including additional diagnostic tests or therapeutic procedures or regimens.

Furthermore, the kit includes an instructional material for use in the diagnosis of an HIV-1-associated neurocognitive disorder in an individual. The instructional material can be a publication, a recording, a diagram, or any other medium of expression which can be used to communicate the usefulness of the method of the invention in the kit for assessment of an HIV-1-associated neurocognitive disorder risk in a individual. The instructional material of the kit of the invention may, for example, be affixed to a container which contains other contents of the kit, or be shipped together with a container which contains the kit. Alternatively, the instructional material may be shipped separately from the container with the intention that the instructional material and the contents of the kit be used cooperatively by the recipient.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Example 1: Detecting HIV-1-Associated Neurocognitive Disorders in Subjects by Measuring the Acetyl Spermine and Acetyl Spermidine Levels in CSF Chemicals:

An AccQ.Fluor kit, which included the AccQ.Fluor derivatizing agent Nhydroxysuccinimidyl-6-aminoquinoyl carbamate, was donated by Waters (Milford, Mass., USA). Acetyl spermidine and acetyl spermine were purchased from Sigma (St. Louis, Mo., USA). The internal standard, 1,7-diaminoheptane, was from Aldrich (Milwaukee, Wis., USA). Eluent A (140 mM acetate, 17 mM triethanolamine, pH 5.05) was used as supplied in the AccQ.Fluor kit. Water was from a Millipore (New Bedford, Mass., USA) Milli-Q system. HPLC-grade acetonitrile was from Fisher Scientific (Springfield, N.J., USA).

Extraction of CSF:

CSF was boiled for 5 minutes to deproteinize before pre-column derivatization.

Pre-Column Derivatization of Samples:

An internal standard (10 µl of 2 µM 1,7-diaminoheptane) was added to 10-60 µl of mixtures of polyamine standards (acetyl spermine, acetyl spermidine) or biological extracts; borate buffer (0.2 M sodium borate, 1 mM EDTA, pH 8.8) was added to produce final volumes of 90 µl. The AccQ. Fluor reagent (10 µl) was added and the sample was mixed and incubated in a 55° C. water bath for 20 minutes to promote derivatization. The 20-minute incubation period was used to assure that the reaction was complete but control experiments demonstrated no gain in signal after a 10-minute incubation. Derivatized samples were analyzed within 24 h.

High-Performance Liquid Chromatography:

The Waters HPLC system included a quaternary pump (Model 625), a system controller (Model 600E), an autosampler (Model 715), and a fluorescence detector (Model 470). The system was controlled and data were collected using Waters Millenium software. The peak-area values reported here were calculated by the Millenium software. A 5-flm silica particle C8 Microsorb-MV column (150×4.6 mm I.D.) with a 100-A pore size (Rainin Instrument, Woburn, Mass., USA) was used for separations. Fluorescence excitation was at 250 nm and emission was detected at 395 nm. All changes in mobile phase were linear from one composition to the next. The flow-rate was 1.0 ml min$^{-1}$. All the analyses were done at room temperature.

Method Validation:

The suitability of the analytical system was assured by demonstrating that acetyl spermidine, acetyl spermine and the internal standard were resolved from each other and from all other potentially interfering peaks in the biological sample extract. Instrument precision was monitored by making triplicate injections into the HPLC system from a single pooled standard. To demonstrate linearity, a series of standard solutions of the two polyamines in water were used to construct calibration curves; the polyamine content of these standards ranged from 0.66 to 40 pmol and 10 pmol of the internal standard, 1,7-diaminoheptane, was included in every injection. To demonstrate recovery of polyamines from a biological matrix, 20 pmol of polyamine standard was added to a CSF sample and the results were compared to an unspiked sample.

Results:

The acetyl spermidine levels in CSF from 10 ANI, 9 MNCD and 11 HAD subjects was measured, as well as that of 10 HIV-infected subjects with normal cognition. The results are shown in FIG. 1. The lowest levels of acetyl spermidine in CSF were found in the control subjects, i.e., the HIV-infected subjects with normal cognition. The acetyl spermidine levels did not significantly increase in ANI subjects as compared to control, as may be seen in FIG. 1. The acetyl spermidine levels did significantly increase in MNCD subjects, and increased yet further in HAD subjects.

Figure 2:
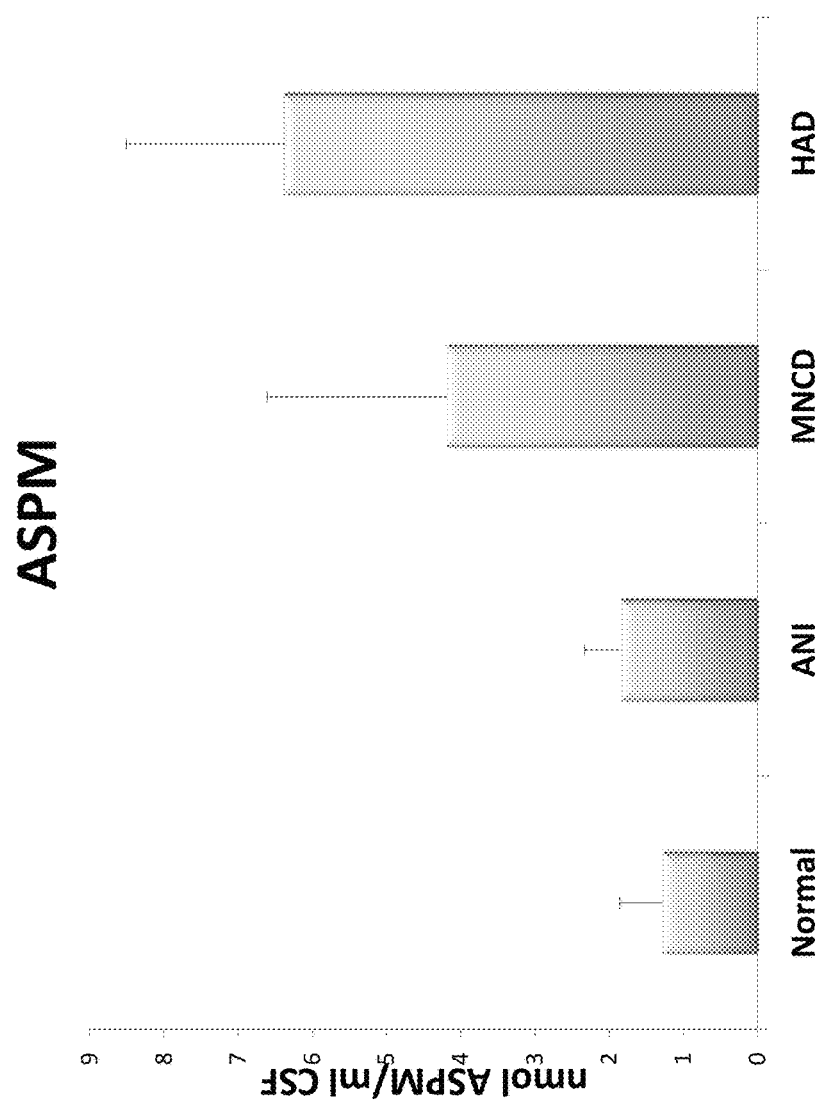
FIG. 2 illustrates the acetyl spermine (ASPM) levels in CSF from 10 ANI, 9 MNCD and 11 HAD subjects as compared to 10 HIV-infected control subjects with normal cognition. The averages are shown. The error bars represent the standard deviation.

The same trend was observed for the acetyl spermine levels in CSF from 10 ANI, 9 MNCD and 11 HAD subjects, as well as that of 10 HIV-infected subjects with normal cognition. The results are shown in FIG. 2. The lowest levels of acetyl spermine in CSF were found in the control subjects. The acetyl spermine levels did not increase significantly in ANI subjects as compared to control, as may be seen in FIG. 2. The acetyl spermine levels did significantly increase in MNCD subjects, and increased yet further in HAD subjects.

Figure 3:
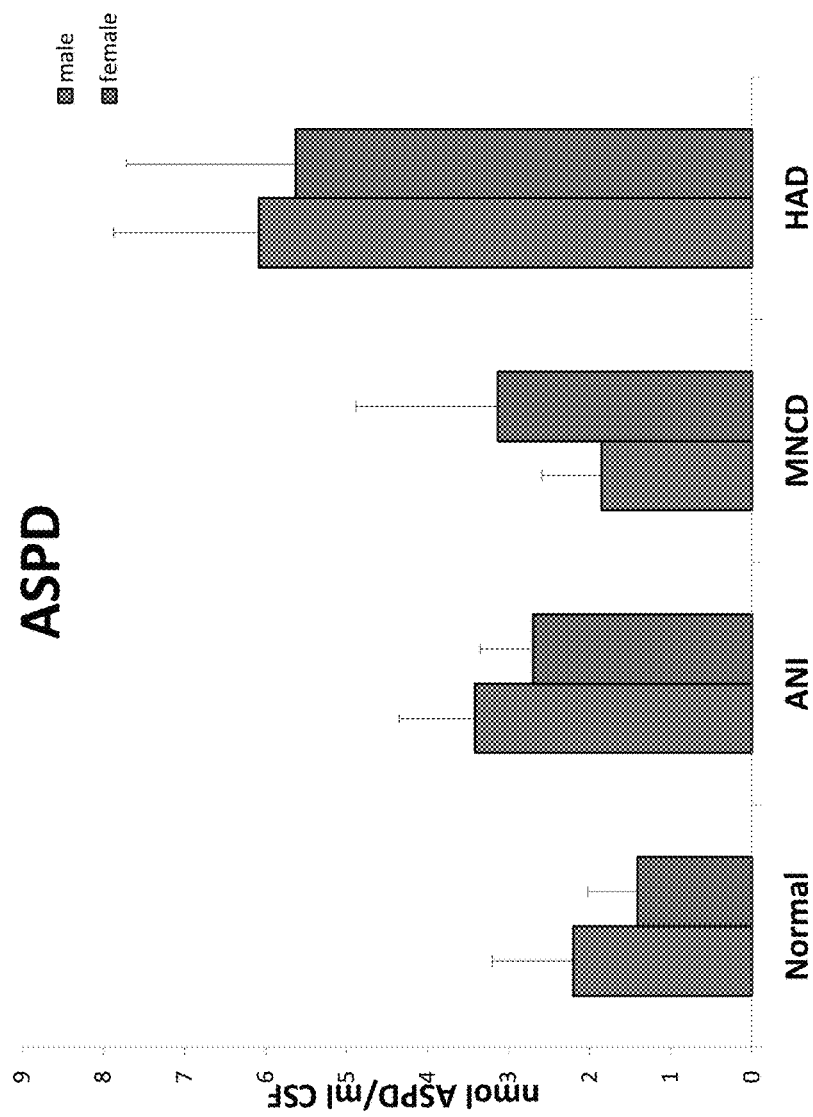
FIG. 3 illustrates the gender differences (males=lighter bars; females=darker bars) in acetyl spermidine levels in HIV-1-associated neurocognitive disorders compared to HIV-infected control individuals with normal cognition. The averages are shown. The error bars represent the standard deviation.

The levels of acetyl spermidine in each group were compared by gender, and the results are shown in FIG. 3. There was no difference between the acetyl spermidine levels of males (open bar) and females (closed bar) in control samples. However, for ANI, MNCD and HAD patients, the acetyl spermidine levels in females were more elevated than in males, as shown in FIG. 3. There was a statistically significant difference in the elevation of the acetyl spermidine levels in ANI, NCD or HAD samples compared to control in females. In males, there was a statistically significant difference in the elevation of the acetyl spermidine levels in NCD and HAD samples compared to control.

Figure 4:
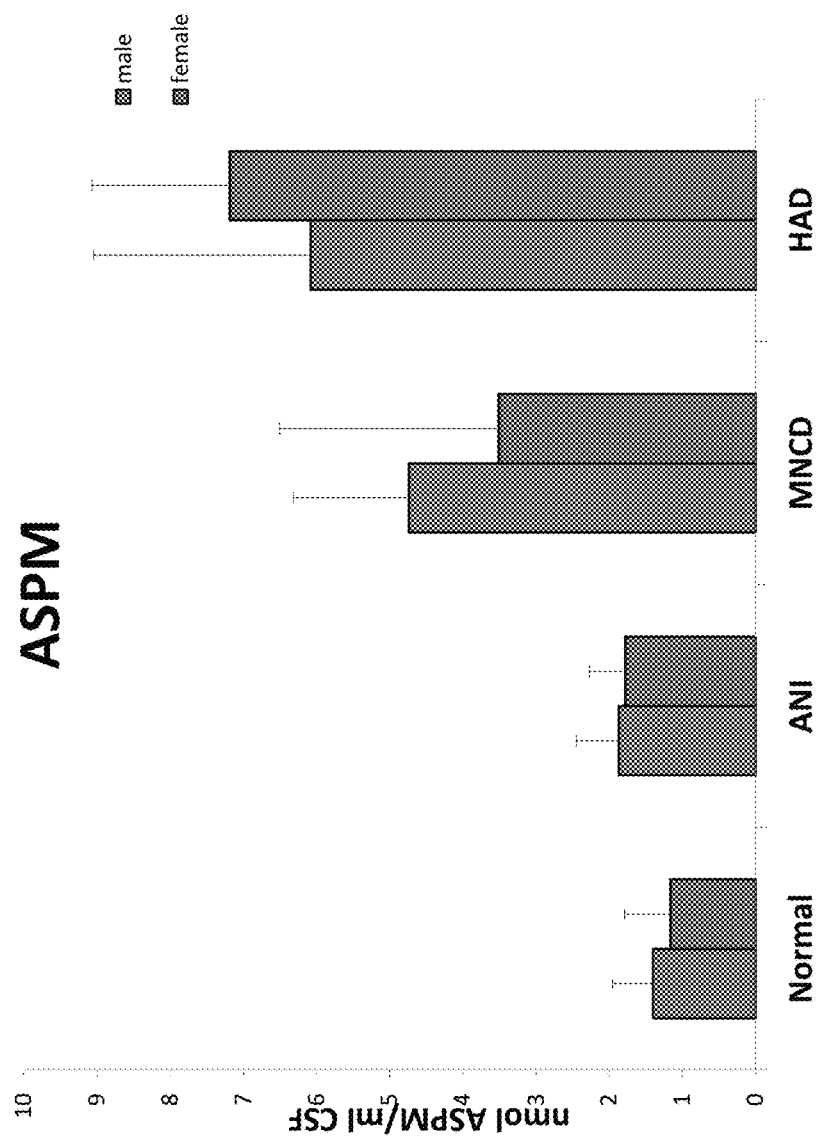
FIG. 4 illustrates the gender differences (males=lighter bars; females=darker bars) in acetyl spermine levels in HIV-1-associated neurocognitive disorders compared to HIV-infected control individuals with normal cognition. The averages are shown. The error bars represent the standard deviation.

The levels of acetyl spermine in each group were also compared by gender, as illustrated in FIG. 4. There was no difference between the acetyl spermine levels of males (open bar) and females (closed bar) in control samples. However, for ANI, MNCD and HAD patients, the acetyl spermine levels in females were more elevated than in males, as shown in FIG. 4. There was a statistically significant difference in the elevation of the acetyl spermine levels in NCD or HAD samples compared to control in females and in males. However, there was no statistically significant difference in the elevation of the acetyl spermine levels in ANI samples compared to control in both genders.

Example 2: Polyamines: Potential Predictive Biomarker for HIV-1-Associated Neurocognitive Disorders The results presented herein show that HIV-1 Tat activates polyamine flux in astrocytes. This flux is generated upon activation of the polyamine catabolic enzyme, spermidine/spermine-N1-acetyltransferase (SSAT) and is also increased in brain samples from subjects with HIV-associated neurocognitive disorders (HAND) as compared to subjects with normal cognition. Polyamine flux consumes acetyl-CoA and generates acetylated polyamines in the milieu. Based on these data, it is believed that the activation of SSAT-driven polyamine flux in the brains of subjects with HAND disseminates acetylated polyamines into the CSF. To test this hypothesis, experiments were performed to assess acetyl-polyamine levels in the CSF of 99 subjects with wide range of HAND severities. The results show that acetylpolyamine levels correlate with HAND severity. Collectively, the data presented herein suggest that polyamine metabolism plays a pivotal role in the neurodegeneration process among HAND patients and serve as a predictive diagnostic biomarker for different severities of HAND.

The materials and methods employed in the experiments disclosed herein are now described.

Material and Methods

Human CSF and Brain Tissue Samples

CSF samples (n=99) were obtained from the Johns Hopkins National Institute of Mental Health (NIMH) Center for Novel Therapeutics of HIV-associated Cognitive Disorders and CNS HIV-1 Anti-Retroviral Therapy Effects Research (CHARTER) of the University of California at San Diego, both under protocols approved by the respective Institutional Review Boards. The subjects' demographic information is shown in Table 1. Participants included 75% male and 25% females, and the CD4+ T-cell counts of all participants ranged between 381-476 cells/mm$^3$. All subjects were African-American with the exception of three female subjects in the No Neurocognitive Impairment (no-NCI) group and one female subject with HAD. Additionally, we obtained frozen brain samples from 9 subjects with and without HAD from the NeuroAIDS Tissue Consortium (NNTC) in accordance with Temple University Human Subjects Protections and the Institutional Review Board.

TABLE 1

Demographic and clinical presentation of HIV subjects in the validation group (n = 99)

| HAND diagnosis | No NCI (n = 25) | ANI (n = 25) | MCMD (n = 24) | HAD (n = 25) |
|---|---|---|---|---|
| Age, years | | | | |
| Mean ± SD | 46.6 (5.1) | 46.0 (3.9) | 48.4 (5.2) | 46.9 (5.3) |
| Median (range) | 47 (37-60) | 46 (39-52) | 49.5 (39-57) | 46 (35-58) |
| Gender | | | | |
| Male (%) | 18 (72) | 17 (68) | 18 (75) | 17 (68) |
| Female (%) | 7 (28) | 8 (32) | 6 (25) | 8 (32) |
| Race | | | | |
| African American | 22 | 25 | 24 | 24 |
| Caucasian | 3 | — | — | 1 |
| CD4 T cell count/μL | | | | |
| Mean ± SD | 537.9 (281.3) | 441.5 (228.1) | 500.8 (260.9) | 447 (229.9) |
| Median (range) | 499 (20-1012) | 381 (174-1052) | 476.5 (25-1056) | 402 (19-973) |

Abbreviations used: HAND = HIV-associated neurocognitive disorders;
No NCI = no neurocognitive impairment;
ANI = asymptomaticneurocognitive impairment;
MCMD = minor cognitive-motor disorder;
HAD = HIV-associated dementia.

Primary Astrocyte Cultures

Human primary astrocytes and neurons were obtained from the Comprehensive NeuroAIDS Center at Temple University. Briefly, fetal brain tissue (gestational age, 16-18 weeks) was obtained from elective abortion procedures performed in full compliance with the National Institutes of Health and Temple University ethical guidelines. Tissue was mechanically and enzymatically dissociated, and astrocyte cultures were obtained by the orbital shaking method to remove other glial cells types. Astrocytes were cultured in growth media containing 10% FBS until confluent. These astrocytes were transduced with adeno-null or Adeno-Tat (Merali S, et al., Journal of chromatography B, Biomedical applications 1996; 675:321-6) [Mukerjee R, Deshmane S L, Fan S, Del Valle L, White M K, Khalili K, Amini S, Sawaya B E. Involvement of the p53 and p73 transcription factors in neuroAIDS. Cell Cycle. 2008 Sep. 1; 7(17):2682-90]. In brief, complete media from primary astrocytes ($3\times10^6$ cells) grown in 10 cm tissue culture plate was removed and then treated with Adenovirus (Null or Tat) at an MOI of 5.0 plaque forming units per cell re-suspend in 1 ml of Optimem medium. After one hour of incubation at 37° C. complete cell culture media was added and cells incubated for 24 h. An additional control included un-transduced astrocytes. The media from these cell cultures was saved and cell were washed in 1×PBS and harvested for polyamine, acetyl polyamines, SSAT and acetyl-CoA analyses. In addition the media was analyzed for acetyl polyamines content.

Analysis for Polyamines and Acetylated Polyamines

The polyamines spermidine, spermine, and putrescine and acetylspermidine were analyzed by HPLC using a fluorescence tag previously shown to react with primary and secondary amines. This method utilizes an activated carbamate, N-hydroxysuccinidyl-6-aminoquinoyl carbamate (AccQ.Fluor), to derivatize the primary and secondary amines, providing stable and highly fluorescent adducts. It has been demonstrated that analysis based on this pre-column derivatization method is quantitative, reproducible, linear and sensitive to 660 fmol (Merali S, et al., Journal of chromatography B, Biomedical applications 1996; 675:321-6). Briefly, the biological samples were deproteinized by heating in a boiling water bath for 2 min. The samples were clarified by centrifugation at 2,000×g for 5 min and the final supernatant was defined as the biological extract. Protein assays were conducted with the BioRad (Melville, N.Y., USA) dye binding assay using bovine serum albumin as the standard. The biological extracts (30 µl) were added to the borate buffer (0.2 M sodium borate, 1 mM EDTA, pH 8.8) for a final volume of 90 µl. The AccQ.Fluor reagent (10 µl) was added, and the samples were mixed and incubated in a 55° C. water bath for 20 min to promote derivatization. For separation, the Waters HPLC system included a separation module (Model 2790) and a multi fluorescence detector (Model 2475). A 5 µm silica particle C8 Microsorb-MV column (150×4.6 mm I.D.) with a pore size of 100 Å was used. Fluorescence excitation was at 250 nm and emission was detected at 395 nm. The mobile-phase elution gradient was conducted as previously described (Merali S, et al., Journal of chromatography B, Biomedical applications 1996; 675:321-6). All changes in the mobile phase were linear from one composition to the next. The flow-rate was 1.0 ml per min. All the analyses were performed at room temperature. The system was controlled and data were collected using Waters Millennium software. The peak-area values were calculated by the Millennium software.

SSAT Activity Measurements

The SSAT activity in biological extracts was calculated by measuring the formation of the acetylspermidine from the added substrates, acetyl Coenzyme A and spermidine, as previously described (Merali S., J Biol Chem 1999; 274: 21017-22 and Moncada C A, et al., J Biol Chem 2008; 283:7690-6). The AccQ.flour tagged substrates and the products were separated by reverse phase HPLC and the amount of acetylspermidine was quantitated by integrating the area under the peak as described above for polyamine analysis. Briefly, the brain tissue in NKP buffer (2.68 mM KCl, 1.47 mM $KH_2PO_4$, 51.1 mM $Na_2HPO_4$, 7.43 mM $NaH_2PO_4$, 62 mM NaCl, 0.05 mM $CaCl_2$, 0.05 mM $MgCl_2$) was ultrasonicated for 5 min at 40 watts and 70% duty cycle (Heat System, Ultrasonics Inc., Plainview, N.Y., USA). A cytosolic fraction was prepared by centrifugation of the homogenate at 100,000×g for 1 hr at 4° C. An aliquot of the supernatant was retained for Bradford protein assay. To the supernatant Spermidine (150 µM) was added to 40 µl supernantant and the enzyme reaction was initiated by addition of 250 µM of acetylCoA at 37° C. The samples were incubated for 10 min and the reaction was terminated by heating in a boiling water bath for 2 min. The sample was clarified by centrifugation at 5,000×g for 5 min. The supernatant was assessed by HPLC analysis using AccQ.Fluor reagent as previously described (Merali S, et al., Journal of chromatography B, Biomedical applications 1996; 675:321-6).

Acetyl-CoA Quantitation Using Capillary Electrophoresis

For acetyl-CoA measurements, the primary astrocytes were lysed and processed using solid-phase extraction as previously described (Kee K, et al., J Biol Chem 2004; 279:40076-83 and Kee K, et al., J Biol Chem 2004; 279: 27050-8). Extracts were analyzed on a Beckman P/ACE MDQ capillary electrophoresis system equipped with a photodiode array detector and an uncoated fused silica CE column. The column was 75 µm in diameter (inner) and 60 cm in length, and there was 50 cm from the inlet to the detection window. The column was preconditioned with 1 M NaOH and Milli-Q water for 10 min each at 20 p.s.i. The column was then equilibrated with 100 mM NaH2PO4 running buffer containing 0.1% α-cyclodextrin (pH 6.0) for 10 min. After each run, the capillary was rinsed with 1 M NaOH, Milli-Q water, and running buffer for 2 min each. The injection was conducted hydrodynamically at a pressure of 0.5 p.s.i. for 10 s. The injection volume was calculated using the CE Expert Lite software from Beckman. The separation voltage was 15 kV at a constant capillary temperature of 15° C. To establish standard calibration curves, solutions containing acetyl-CoA and the internal standard (isobutyryl-CoA, 41 nM) were prepared at concentrations ranging from 1 to 200 nM. Standards were processed as described above for cell lysates and suspended in 10 µl of water. Coenzyme was monitored with a photodiode array detector at the maximum absorbance wavelength (253.5 nm). Data was collected and processed using Beckman P/ACE 32 Karat software version 4.0. Cellular acetyl-CoA levels were expressed as nmoles/mg protein.

Statistical Analysis

All of the data were analyzed using Prism 6 (GraphPad Software Inc., La Jolla, Calif., USA). The significant differences between the cohorts were assessed by Kruskal-Wallis and Dunn's post multiple comparison tests. The Mann-Whitney U test (with Bonferroni correction) was used to compare the differences between the two groups. We elected to use nonparametric tests for the clinical data because of the skewed data distribution. For the parametric data, we used one-way ANOVA with post hoc Tukey-Kramer test to compare the groups. For several in vitro assays, we used the unpaired t test; the results were expressed as the mean±SEM.

The results of the experiments presented in this Example are now described.

Figure 5A:
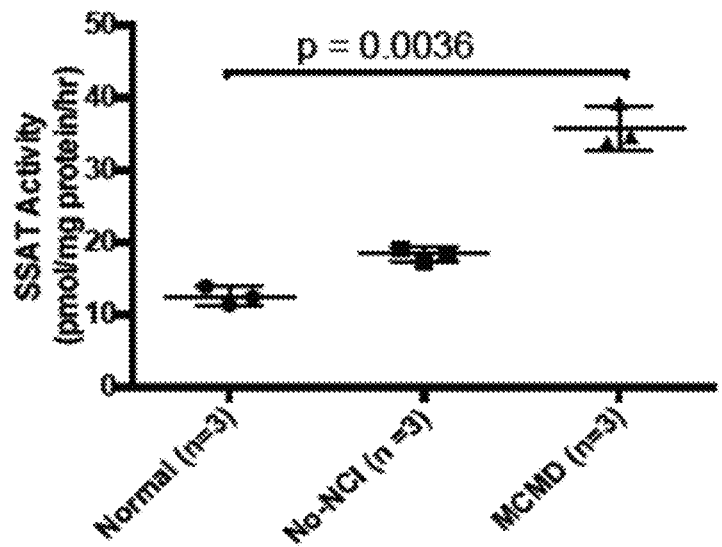
FIGS. 5A and 5B, is a series of images demonstrate that the elevation of SSAT positively correlates with the levels of acetylated polyamines.
Figure 5B:
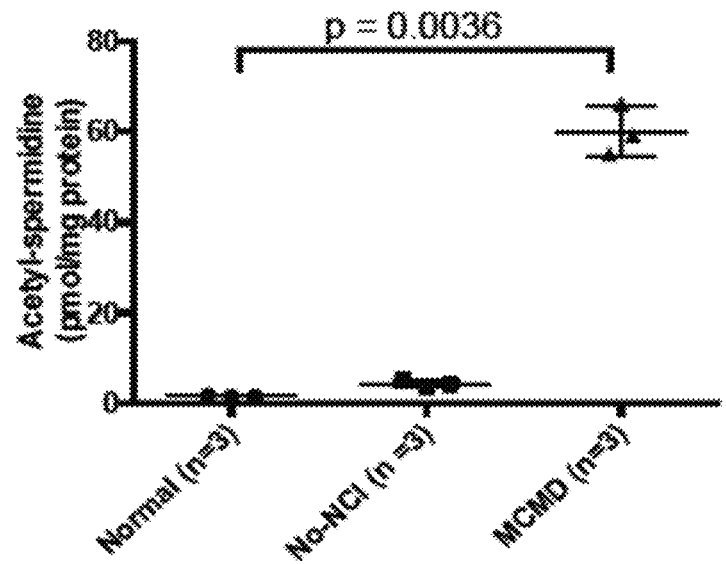

SSAT Driven Polyamine Flux is Increased in Brain Samples from Subjects with HAND Microarray studies show an increase in SSAT gene expression in response to HIV-1 Tat over-expression in immature dendritic cells (Izmailova E, et al., Nat Med 2003; 9:191-7). However, very little is known about enzymatic activity of SSAT in the brains of patients with HAND. To address this gap in knowledge, SSAT activity was measured in brain lysates from HIV patients with MCMD (n=3) and compared them to subjects with no-NCI (n=3) or normal no-HIV controls (n=3). Significant elevation of SSAT activity was detected in MCMD (FIG. 5A). Since an increase in SSAT activity could trigger an increase polyamine metabolic flux (Kramer D L, et al., J Biol Chem 2008; 283:4241-51), experiments were designed to test this possibility and showed as compared to no-NCI and normal control, the acetylspermidine levels were increased MCMD (FIG. 5B), while the polyamine levels remained unchanged (Table 2A).

TABLE 2A

Polyamine levels in the brain are unchanged indicating that polyamine flux is enhanced. (No-HIV, n = 3; no-NCI, n = 3; MNCD, n = 3)

|  | Putrescine (pmol/mg tissue) | Spermine (pmol/mg tissue) | Spermidine (pmol/mg tissue) |
| --- | --- | --- | --- |
| No-HIV | 18 ± 4.1 | 162 ± 11 | 549 ± 31 |
| NCI | 20 ± 3.2 | 171 ± 15 | 538 ± 46 |
| MCMD | 35 ± 3.8 | 182 ± 24 | 522 ± 22 |

Acetylpolyamines are Released from Astrocytes

Figure 6A:
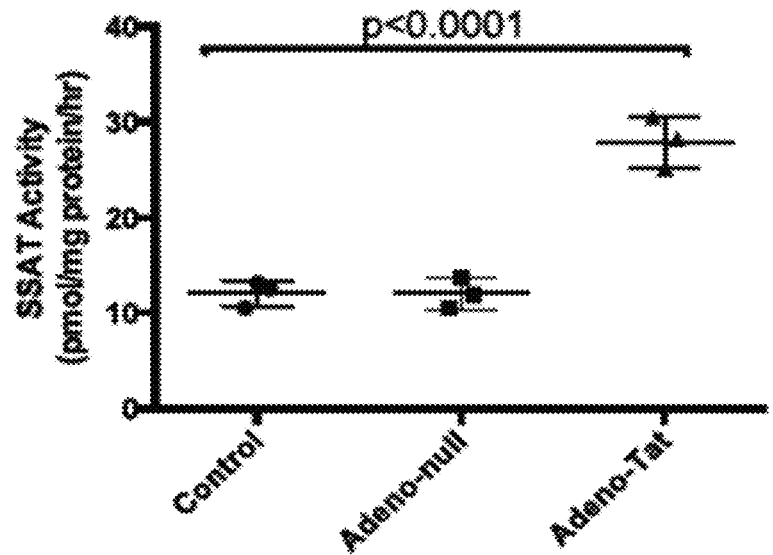
FIGS. 6A and 6B, is a series of images that demonstrate that acetylpolyamines are released from astrocytes.
Figure 6B:
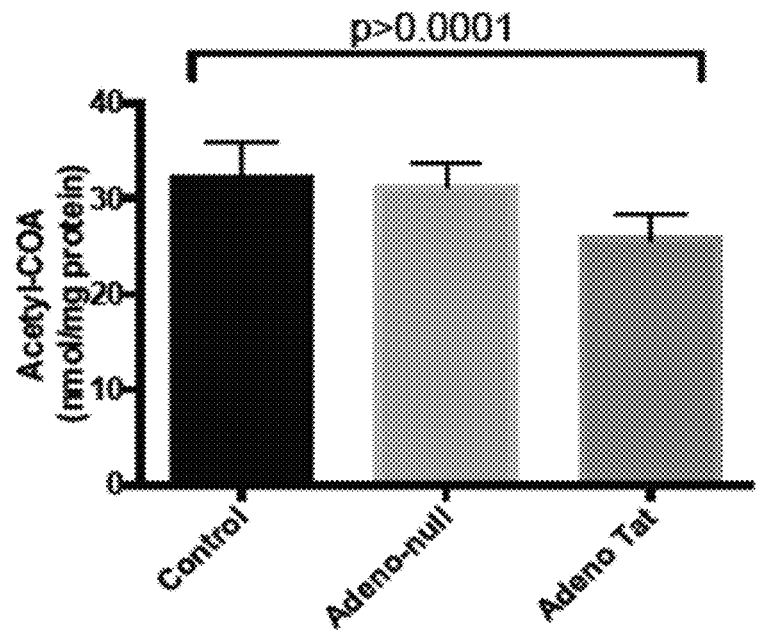

Astrocytes are known to play a significant role in the neuropathology of HAND. Hence, experiments were designed to investigate whether polyamine flux can trigger the release of acetylated polyamines from human primary astrocytes expressing HIV-1 Tat. The results show that the expression of Tat increased SSAT activity by approximately 3-fold in human primary astrocytes compared to untransduced astrocytes or astrocytes transduced with adeno-null (FIG. 6A). Similar to brain tissue in HAD patients, the increase in SSAT activity may have contributed to increased polyamine metabolic flux, resulting in the decrease in the SSAT substrate acetyl-CoA and unchanged levels of polyamines. Experiments were designed to test these two possibilities by measuring acetyl-CoA levels and polyamines (Kee K, et al., J Biol Chem 2004; 279:27050-8) in the same lysates used for measuring SSAT activity. The high-pressure capillary electrophoresis analysis of acetyl-CoA pools showed about 25% decrease in this SSAT substrate when the primary astrocytes were transduced to overexpress HIV-1 Tat as compared to null-transduction and normal controls (FIG. 6B). As expected, polyamine levels were unchanged Tat expressing astrocytes compared to controls (Table 2B). The acetylation of polyamines decreases their positive charge, thereby increases the possibility for export of polyamines from cells. To evaluate this possibility, the acetylated spermidine and acetylated spermine levels were quantitated in the media of the cells transduced with HIV-1 Tat and controls. Tat expression induced increased acetylation of both spermidine and spermine compared to the controls (Table 2C). Taken together, these data support the hypothesis that Tat-induced increase in SSAT ratchets the polyamine flux and causes an increase in the acetylated polyamines and a decrease in the acetyl-CoA.

TABLE 2B

Effect of HIV-1 Tat on polyamine levels. Results are presented from three independent experiments (mean ± SD)

|  | Putrescine (mM) | Spermidine (mM) | Spermine (mM) |
| --- | --- | --- | --- |
| Control | 0.41 ± 0.15 | 0.79 ± 0.25 | 1.10 ± 0.21 |
| Adeno-null | 0.45 ± 0.32 | 0.82 ± 0.45 | 1.24 ± 0.35 |
| Adeno-Tat | 0.61 ± 0.39 | 0.75 ± 0.36 | 0.95 ± 0.33 |

TABLE 2C

Increased acetylated polyamines levels in the media of primary astrocytes transduced with HIV-1 Tat

|  | Acetyl-Spermine (pmol/ml) | Acetyl-spermidine (pmol/ml) |
| --- | --- | --- |
| Control | 1.5 (DL) | 1.5 (DL) |
| Adeno-null | 1.5 (DL) | 1.5 (DL) |
| Adeno-Tat | 3.2 ± 1.6 | 5.2 ± 2.1 |

DL = Detection limit

Acetylated Polyamine Levels are Increased in the CSF of the Patients with HAND

Figure 7:
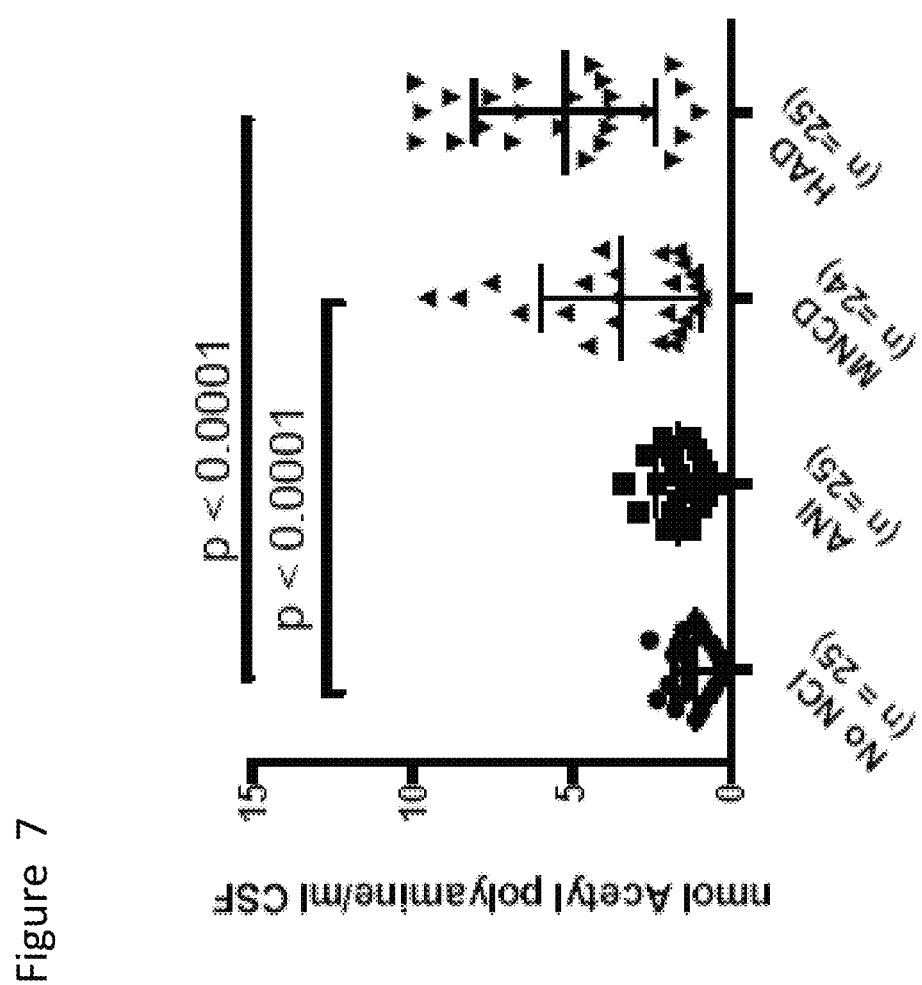
FIG. 7 is an image showing acetylpolyamine levels in the CSF of the validation study (n=99) consisting of No-NCI, ANI, MCMD, HAD. Acetylspermine levels are significantly elevated in MCMD and HAD groups compared to the no NCI and ANI groups ($p<0.0001$ using Kruskal-Wallis test).

In view of the fact that the data showed an increase in the acetylated polyamine pools both in the brain tissue of patients with MCMD and in the media of HIV-1 Tat transduced astrocytes, it was hypothesized that the levels of acetylated polyamines would also be increased in the CSF of patients with HAND. To test this hypothesis, experiments were designed to assess acetyl-polyamine levels in the CSF of three groups of subjects with different HAND severity i.e. ANI (n=25), MCMD (n=24) and HAD (n=25) and compared them to no NCI (n=25) HIV+ participants. All the groups totaling 99 participants were matched for age, gender, race and CD4+ T cell count (Table 1). The results show significant increases in acetylpolyamine levels in HAD compared to no NCI and ANI ($p<0.0001$) and between MCMD and no NCI and ANI ($p<0.0001$) (FIG. 7). Collectively, these results suggest that the levels of acetylated polyamine increase with the degree of HAND severity in CSF.

Biomarker for HIV-1-Associated Neurocognitive Disorders

Figure 8:
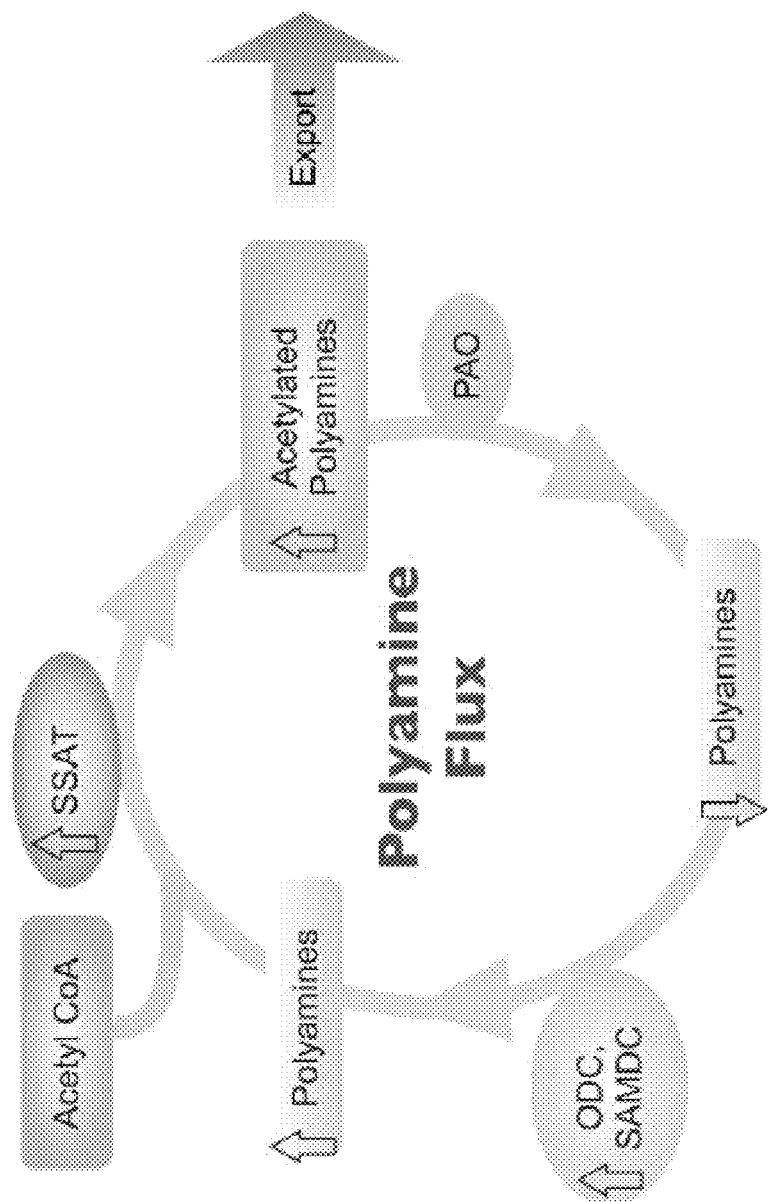
FIG. 8 is a schematic of a proposed metabolic ratchet model for polyamine flux. Increased SSAT initiates polyamine flux by acetylation of polyamines, which facilitates their export from the cell. Acetylation eliminates the ability of polyamines to repress biosynthetic enzymes (ODC and SAMDC), which leads to a compensatory increase in polyamine biosynthesis. The restored polyamine pools are then available for SSAT acetylation and continuation of the cycle. When flux increases, substrate utilization (such as acetyl-CoA) and product accumulation (such as acetylated polyamines) also increase but the levels of polyamines do not change. Our results show that induction of SSAT in astrocytes by HIV Tat leads to depletion of acetyl-CoA pools and accumulation of acetylated polyamines, a critical consequence of increased cycling. Abbreviations: ODC, Ornithine Decarboxylase; SAMDC, S-Adenosylmethionine Decarboxylase; PAO, Polyamine Oxidase.

Polyamines are known to enhance HIV-1 reverse transcription in vitro (Zhang H, et al., Journal of virology 1996; 70:2809-24). Furthermore, SSAT, a rate-limiting enzyme in polyamine catabolism has been implicated in HIV-1 pathogenesis. For example, it has been reported that SSAT expression is elevated in the Flp-In TREx 293 cell line overexpressing the HIV protein Vpr (Yoshizuka N, et al., Journal of virology 2005; 79:11366-81). Moreover, studies using the yeast two hybrid system and immature dendritic cells show that both Vif and Tat, respectively can modulate the SSAT activity to impact the polyamine levels (Izmailova E, et al., Nat Med 2003; 9:191-7 and Lake J A, et al., Journal of clinical virology: the official publication of the Pan American Society for Clinical Virology 2003; 26:143-52). However, the status of SSAT and its metabolic products in brain tissue and CSF were not known. The results presented herein are believed to be the first that shows SSAT activity is elevated in brain tissue from HIV patients compared to uninfected controls, and this elevation is potentiated in patients with HAND. Further, the results presented herein demonstrate that the elevation of SSAT positively correlates with the levels of acetylated polyamines (FIG. 5). Previous studies have shown that the increase in SSAT activity influences polyamine homeostasis by modulating polyamine metabolic flux (Kramer D L, et al., J Biol Chem 2008; 283:4241-51) (FIG. 8). The consequences of polyamine flux are to maintain polyamine levels at the cost of increased consumption of precursors i.e. acetyl-CoA which continues as long as SSAT levels are above baseline. The flux also generates more products such as acetylated polyamines. Based on these findings and because neurotoxic insults by HIV have been shown to disrupt glial NMDA receptor/polyamine interactions, it is believed that the acetylated polyamines are elevated in the CSF of HAND patients. To test this hypothesis, experiments were designed to investigate the possibility of polyamine flux in human primary astrocytes transduced with HIV-1 Tat. Astrocytes were chosen because these cells are believed to have a significant role in the neuropathology of HAND (Borjabad A, et al., Journal of neuroimmune pharmacology: the official journal of the Society on NeuroImmune Pharmacology 2010; 5:44-62). Astrocytes have been shown to have a complex bidirectional relationship with adjacent neurons and they play neurotrophic and pro-apoptotic roles (Araque A, et al., Philosophical transactions of the Royal Society of London Series B, Biological sciences 2010; 365:2375-81). The concept of the tripartite synapse has been suggested in which astrocytes not only perform housekeeping functions but also sense neurotransmitter release through the coincident release of gliotransmitters such as calcium, glutamate, nitric oxide, polyamines and biogenic amines (Tewari S G, et al., Journal of biological physics 2012; 38:465-96). In patients with HIV, dysregulation of these molecules may play key roles in HAND (Kaul M, et al., Nature 2001; 410:988-94 and Hult B, et al., International review of psychiatry 2008; 20:3-13). The data presented herein show that while polyamines levels were unchanged, acetyl-CoA levels are depleted and the acetylated polyamines are increased intracellularly and in the media of the astrocytes transduced with HIV-1 Tat. Collectively, these data support the increase in the polyamine flux in astrocyte transduced with HIV-1 Tat. The results presented herein demonstrate that polyamine levels are not altered but acetyl-CoA levels are decreased. Because acetyl-CoA is a sensor of the rate of glucose metabolism (Liu C, et al., Amino Acids 2014; 46: 701-715), the alteration of acetyl CoA levels is likely to impact glycolysis and lactate production. In other words, the polyamine flux may shift the glucose metabolism towards pyruvate and away from lactate resulting in decreased in lactate levels. This effect is likely to impact the astrocyte-neuron lactate shuttle and cause neuronal metabolic dysfunction.

The data supporting enhanced polyamine flux both in the brain tissue of subjects with HAD as compared to normal controls and astrocytes transduced to over-express HIV-1 Tat prompted the investigation of the levels of these acetylated polyamines in the CSF of patients with and without HAND. The data presented herein show that acetylated polyamines are increased in patients with HAD compared to HIV patients with normal cognitive functions and that these changes correlated with the severity of HAND.

The results presented herein demonstrate proof of principal for the impact of Tat on astrocytes, since these cells were assessed in isolation. Experiments can be designed to investigate the effects of Tat exposure on neurotransmitter release in the context of the tripartite synapse. A second consideration of the study relates to other diseases that may influence NMDA neurotransmitter levels that may be affected by polyamine flux and acetylation state. For example, major depressive disorder, Alzheimer's, insulin deficiency and others are believed to influence this pathway in the CNS. Co-morbidities including metabolic disorders may influence this pathway, as well. However, it is believed that patients included in this study were not diagnosed with diseases known to impact polyamine flux and acetylation.

In summary, enhanced levels of acetylated polyamine in HIV patients with more severe neurocognitive impairment suggests a potential role for these metabolites in the neurodegeneration process among HAND patients. Thus, polyamine may serve as a potential predictive diagnostic biomarker for different severities of HAND.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of detecting and treating mild neurocognitive disturbance (MNCD) or HIV associated dementia (HAD) in a patient comprising:
    (a) detecting the level of acetyl spermine and/or acetyl spermidine from a biological test sample of said patient; and
    (b) (i) comparing said level of acetyl spermine and/or acetyl spermidine in said test sample to the level of acetyl spermine and/or acetyl spermidine in a biological control sample; wherein an elevated level of acetyl spermine and/or acetyl spermidine in said test sample as compared to the level in said control sample indicates that the patient suffers from mild neurocognitive disturbance or HIV associated dementia; or
        (ii) comparing said level of acetyl spermine and/or acetyl spermidine in said test sample to a standard value or standard value range for mild neurocognitive disturbance or HIV associated dementia;
    wherein a level of acetyl spermine and/or acetyl spermidine that is similar to that of said standard value or that fits within said standard value range for mild neurocognitive disturbance or HIV associated dementia indicates that the patient suffers from mild neurocognitive disturbance or HIV associated dementia; and
    (c) administering a treatment based on the disease status.

2. The method of claim 1 wherein said acetyl spermine and/or said acetyl spermidine level is detected by HPLC, mass spectroscopy or chromogenic sensing.

3. The method of claim 1 wherein said acetyl spermine and/or said acetyl spermidine is derivatized prior to being detected.

4. The method of claim 1 wherein said control sample is from a healthy subject without neurocognitive impairment or an HIV-1-infected subject without neurocognitive impairment.

5. The method of claim 1 wherein mild neurocognitive disturbance is detected.

6. The method of claim 1 wherein HIV associated dementia is detected.

7. The method of claim 1 wherein a level of said acetyl spermidine in said test sample that is from about 1.5-fold to about 2.5-fold that of the control sample indicates that the patient suffers from mild neurocognitive disturbance.

8. The method of claim 1 wherein a level of said acetyl spermidine in said test sample that is greater than about 2.6-fold that of the control sample indicates that the patient suffers from HIV-1-associated neurocognitive disorder.

9. The method of claim 1 wherein a level of said acetyl spermine in said test sample that is from about 3.0-fold to about 4.5-fold that of the control sample indicates that the patient suffers from mild neurocognitive disturbance.

10. The method of claim 1 wherein a level of said acetyl spermine in said test sample that is greater than about 4.6-fold that of the control sample indicates that the patient suffers from HIV associated dementia.

11. The method of claim 1 wherein a sum of the levels of said acetyl spermidine and said acetyl spermine in said test sample that is from about 2.5-fold to about 4.0-fold that of the control sample indicates that the patient suffers from mild neurocognitive disturbance.

12. The method of claim 1 wherein a sum of the levels of said acetyl spermidine and said acetyl spermine in said test sample that is greater than about 4.1-fold that of the control sample indicates that the patient suffers from HIV associated dementia.

13. The method of claim 1 wherein the control value for lack of neurocognitive impairment is 1.3 nmol/ml CSF for acetyl spermine, 1.8 nmol/ml CSF for acetyl spermidine or 3.1 nmol/ml CSF for the sum of acetyl spermidine and acetyl spermine.

14. The method of claim 1 wherein said acetyl spermine standard value for mild neurocognitive disturbance is from about 4.2 nmol/ml to about 6.0 nmol/ml CSF.

15. The method of claim 1 wherein said acetyl spermine control standard for HIV associated dementia is at least about 6.2 nmol/ml CSF.

16. The method of claim 1 wherein said acetyl spermidine standard for mild neurocognitive disturbance is from about 3.0 nmol/ml to about 4.0 nmol/ml CSF.

17. The method of claim 1 wherein said acetyl spermidine standard value for HIV associated dementia is at least about 5.0 nmol/ml CSF.

18. The method of claim 1 wherein said standard value for the sum of acetyl spermidine and acetyl spermine for mild neurocognitive disturbance is from about 7.2 nmol/ml to about 10.0 nmol/ml CSF.

19. The method of claim 1 wherein said standard value for the sum of acetyl spermidine and acetyl spermine for HIV associated dementia is at least about 11.2 nmol/ml CSF.

20. The method of claim 1 wherein said patient is female.

21. A method for monitoring the progression or improvement and treating of an HIV-1-associated neurocognitive disorder (HAND) in a patient comprising:
measuring the level of acetyl spermine and/or acetyl spermidine from a first cerebrospinal fluid test sample of said patient at a first time point;
and measuring the level of acetyl spermine and/or acetyl spermidine from a second cerebrospinal fluid test sample of said patient at a second time point;
wherein an elevated level of acetyl spermine and/or acetyl spermidine in said second test sample compared to the level of acetyl spermine or acetyl spermidine in said first test sample indicates that the HIV-1-associated neurocognitive disorder in said patient has progressed;
wherein a lower level of the acetyl spermine and/or acetyl spermidine in the second test sample compared to the level of acetyl spermine or acetyl spermidine in the first test sample indicates that the HIV-1-associated neurocognitive disorder in the patient has improved; and
wherein an unchanged level of the acetyl spermine and/or acetyl spermidine in the second test sample compared to the level of acetyl spermine or acetyl spermidine in the first test sample indicates that the HIV-1-associated neurocognitive disorder in the patient has not changed; and administering a treatment based on the disease status.

22. The method of claim 21 wherein said acetyl spermine and/or said acetyl spermidine is detected by HPLC, mass spectroscopy or chromogenic sensing.

23. The method of claim 22 wherein said acetyl spermine and/or said acetyl spermidine is derivatized prior to being detected.

24. The method of claim 21 wherein said HIV-1-associated neurocognitive disorder is mild neurocognitive disturbance.

25. The method of claim 21 wherein said HIV-1-associated neurocognitive disorder is HIV associated dementia.

26. The method of claim 21 wherein said patient is female.

27. A method for staging and treating an HIV-1-associated neurocognitive disorder (HAND) in an HIV patient comprising:
measuring the level of acetyl spermine and/or acetyl spermidine in a cerebrospinal fluid test sample of a patient; and
comparing said level of acetyl spermine and/or acetyl spermidine to the level of acetyl spermine and/or acetyl spermidine in a sample of a control person without said HIV-1-associated neurocognitive disorder, a control from a person with a certain known stage of progression of said HIV-1-associated neurocognitive disorder, or to a series of standard values indicative of said stages;
determining which control sample or control standard has the most similar level of acetyl spermine or acetyl spermidine to that of said patient; and
assigning to said patient the stage of said control sample or standard value with the most similar level of acetyl spermine or acetyl spermidine to that of said patient; and
administering a treatment based on the disease status.

28. The method of claim 27 wherein said acetyl spermine and/or said acetyl spermidine is detected by HPLC, mass spectroscopy or chromogenic sensing.

29. The method of claim 28 wherein said acetyl spermine and/or said acetyl spermidine is derivatized prior to being detected.

30. The method of claim 27 wherein said HIV-1-associated neurocognitive disorder is mild neurocognitive disturbance or HIV associated dementia.

31. The method of claim 27 wherein the certain known stage of progression of said HIV-1-associated neurocognitive disorder is mild neurocognitive disturbance or HIV associated dementia.

32. The method of claim 27 wherein said patient is female.

33. A method of detecting and treating asymptomatic neurocognitive impairment (ANI) in a patient comprising:
detecting the level of acetyl spermidine from a cerebrospinal fluid test sample of said patient;
comparing said level of acetyl spermidine in said test sample to the level of acetyl spermidine in a control sample or to a standard value for acetyl spermidine;
wherein an elevated level of acetyl spermidine in said test sample as compared to the level in said control sample or a level of acetyl spermidine that is similar to that of said standard value indicates that the patient suffers from asymptomatic neurocognitive impairment; and
administering a treatment based on the disease status.

34. The method of claim 33 wherein said acetyl spermidine is detected by HPLC, mass spectroscopy or chromogenic sensing.

35. The method of claim 34 wherein said acetyl spermidine is derivatized prior to being detected.

36. The method of claim 33 wherein said control sample is from a healthy subject without neurocognitive impairment or an HIV-1-infected subject without neurocognitive impairment.

37. The method of claim 33 wherein said level of said acetyl spermidine in said test sample that is from about 1.5-fold to about 2.5-fold that of the control sample indicates that the patient suffers from asymptomatic neurocognitive impairment.

38. The method of claim 33 wherein said standard value for lack of neurocognitive impairment is about 1.5 nmol/ml of cerebrospinal fluid.

39. The method of claim 33 wherein said standard value for asymptomatic neurocognitive impairment is from about 2.5 nmol/ml to about 3 nmol/ml of cerebrospinal fluid.

40. The method of claim 33 wherein said patient is female.

41. A method of diagnosing and treating different severities of HIV-associated neurocognitive disorders in a patient, the method comprising detecting an enhanced level of acetylated polyamine in the patient compared to the level of acetylated polyamine in a comparator control; and administering a treatment based on the severity of the disease.

42. The method of claim 41, wherein different severities of HIV-associated neurocognitive disorders is selected from the group consisting of asymptomatic neurocognitive impairment (ANI), mild cognitive and motor disorders (MCMD), and HIV-1 associated dementia (HAD).

43. The method of claim 41, wherein the acetylated polyamine is selected from the group consisting of acetyl spermine, acetyl spermidine, any a combination thereof.

44. The method of claim 41, wherein acetylated polyamine is detected in a biological sample isolated from the patient.

* * * * *